United States Patent
Silvestrini

(10) Patent No.: US 10,350,058 B2
(45) Date of Patent: *Jul. 16, 2019

(54) IN SITU ADJUSTABLE OPTICAL MASK

(71) Applicant: AcuFocus, Inc., Irvine, CA (US)

(72) Inventor: Thomas A. Silvestrini, Alamo, CA (US)

(73) Assignee: AcuFocus, Inc., Irvine, CA (US)

( * ) Notice: Subject to any disclaimer, the term of this patent is extended or adjusted under 35 U.S.C. 154(b) by 64 days.

This patent is subject to a terminal disclaimer.

(21) Appl. No.: 15/436,150

(22) Filed: Feb. 17, 2017

(65) Prior Publication Data

US 2017/0156850 A1 Jun. 8, 2017

Related U.S. Application Data

(60) Continuation of application No. 14/961,308, filed on Dec. 7, 2015, now Pat. No. 9,603,704, which is a
(Continued)

(51) Int. Cl.
*A61F 2/16* (2006.01)
*A61F 2/14* (2006.01)
(Continued)

(52) U.S. Cl.
CPC .............. *A61F 2/1659* (2013.01); *A61F 2/14* (2013.01); *A61F 2/15* (2015.04); *G02F 1/009* (2013.01);
(Continued)

(58) Field of Classification Search
CPC ........ A61F 2/1613; A61F 2/15; A61F 2/1648; A61F 2002/009; A61F 2002/1697; A61F 2/1659; G02C 7/102; G02C 7/046
See application file for complete search history.

(56) References Cited

U.S. PATENT DOCUMENTS

| 564,518 A | 7/1896 | Heilborn |
|---|---|---|
| 1,034,516 A | 8/1912 | Samberg |

(Continued)

FOREIGN PATENT DOCUMENTS

| AR | 241 330 | 12/1992 |
|---|---|---|
| AR | 241 830 | 12/1992 |

(Continued)

OTHER PUBLICATIONS

Accomodation and acuity under night-driving illumination levels. Arumi et al. Ophthal. Physiol. Opt. vol. 17, No. 4, pp. 291-299, 1997.
(Continued)

*Primary Examiner* — David H Willse
*Assistant Examiner* — Tiffany P Shipmon
(74) *Attorney, Agent, or Firm* — Knobbe, Martens, Olson & Bear, LLP

(57) ABSTRACT

Implantable corneal and intraocular implants such as a mask are provided. The mask can improve the vision of a patient, such as by being configured to increase the depth of focus of an eye of a patient. The mask can include an aperture configured to transmit along an optical axis substantially all visible incident light. The mask can further include a transition portion that surrounds at least a portion of the aperture. This portion can be configured to switch from one level of opacity to another level of opacity through the use of a controllably variable absorbance feature such as a switchable photochromic chromophore within a polymer matrix.

22 Claims, 12 Drawing Sheets

Related U.S. Application Data division of application No. 13/802,340, filed on Mar. 13, 2013, now Pat. No. 9,204,962.

(51) Int. Cl.

| | | |
|---|---|---|
| *G02F 1/15* | (2019.01) | |
| *G03C 1/73* | (2006.01) | |
| *G02F 1/00* | (2006.01) | |
| *G02F 1/01* | (2006.01) | |
| *G02C 7/04* | (2006.01) | |

(52) U.S. Cl.
CPC .......... *G02F 1/0126* (2013.01); *G02F 1/0147* (2013.01); *G02F 1/15* (2013.01); *G03C 1/73* (2013.01); *G03C 1/733* (2013.01); *A61F 2002/1696* (2015.04); *G02C 7/046* (2013.01); *G02F 2202/022* (2013.01); *G02F 2202/08* (2013.01); *G02F 2202/14* (2013.01); *G02F 2203/48* (2013.01)

(56) References Cited

U.S. PATENT DOCUMENTS

| | | | |
|---|---|---|---|
| 1,206,132 A | 11/1916 | Otte | |
| 1,959,915 A | 5/1934 | Guthrie | |
| 2,129,305 A | 9/1938 | Feinbloom | |
| 2,350,421 A | 6/1944 | Schoder et al. | |
| 2,470,927 A | 5/1949 | Hale, Jr. | |
| 2,714,721 A | 8/1955 | Stone, Jr. | |
| 3,034,403 A | 5/1962 | Neefe | |
| 3,074,407 A | 1/1963 | Moon et al. | |
| 3,270,099 A | 8/1966 | Camp | |
| 3,339,997 A | 9/1967 | Wesley | |
| 3,392,727 A | 7/1968 | Hanlon | |
| D212,868 S | 12/1968 | Olson | |
| 3,458,870 A | 8/1969 | Stone, Jr. | |
| 3,507,566 A | 4/1970 | Knapp | |
| 3,536,386 A | 10/1970 | Spivack | |
| 3,578,850 A | 5/1971 | Grant | |
| 3,600,098 A | 8/1971 | Mohrman | |
| 3,726,587 A | 4/1973 | Kendall | |
| 3,776,230 A | 12/1973 | Neefe | |
| 3,794,414 A | 2/1974 | Wesley | |
| 3,852,032 A | 12/1974 | Urbach | |
| 3,877,502 A | 4/1975 | Hunckler | |
| 3,914,013 A | 10/1975 | Rosenberg | |
| 3,918,972 A | 11/1975 | Evens et al. | |
| 3,946,982 A | 3/1976 | Calkins et al. | |
| 3,982,541 A | 9/1976 | L'Esperance, Jr. | |
| 4,010,496 A | 3/1977 | Neefe | |
| 4,026,869 A | 5/1977 | Evens et al. | |
| 4,073,015 A | 2/1978 | Peyman | |
| 4,099,529 A | 7/1978 | Peyman | |
| 4,116,439 A | 9/1978 | Chavarria et al. | |
| 4,138,191 A | 2/1979 | Peyman | |
| 4,191,195 A | 3/1980 | Miller | |
| 4,210,391 A | 7/1980 | Cohen | |
| 4,272,191 A | 6/1981 | Bergkvist | |
| 4,298,004 A | 11/1981 | Schchar et al. | |
| 4,312,575 A | 1/1982 | Peyman et al. | |
| 4,340,283 A | 7/1982 | Cohen | |
| 4,367,949 A | 1/1983 | Layering | |
| 4,383,843 A | 5/1983 | Iyengar | |
| 4,402,579 A | 9/1983 | Poler | |
| 4,402,681 A | 9/1983 | Haas et al. | |
| 4,409,979 A | 10/1983 | Roussel et al. | |
| 4,423,728 A | 1/1984 | Lieberman | |
| 4,445,892 A | 5/1984 | Hussein et al. | |
| 4,450,593 A | 5/1984 | Poler | |
| 4,452,235 A | 6/1984 | Reynolds | |
| 4,461,294 A | 7/1984 | Baron | |
| 4,469,098 A | 9/1984 | Daui | |
| 4,485,499 A | 12/1984 | Castleman | |
| 4,505,855 A | 3/1985 | Bruns et al. | |
| 4,528,311 A | 7/1985 | Beard et al. | |
| 4,536,240 A | 8/1985 | Winn | |
| 4,538,608 A | 9/1985 | L'Esperance, Jr. | |
| 4,547,914 A | 10/1985 | Castleman | |
| 4,547,915 A | 10/1985 | Castleman | |
| 4,563,565 A | 1/1986 | Kampfer et al. | |
| 4,573,998 A | 3/1986 | Mazzocco | |
| 4,575,373 A | 3/1986 | Johnson | |
| 4,575,915 A | 3/1986 | Clark et al. | |
| 4,576,453 A | 3/1986 | Borowsky | |
| 4,582,402 A | 4/1986 | Knapp | |
| 4,607,617 A | 8/1986 | Choyce | |
| 4,612,012 A | 9/1986 | White | |
| 4,615,702 A | 10/1986 | Koziol et al. | |
| 4,617,023 A | 10/1986 | Peyman | |
| 4,624,669 A | 11/1986 | Grendahl | |
| 4,633,866 A | 1/1987 | Peyman et al. | |
| 4,636,049 A | 1/1987 | Blaker | |
| 4,636,211 A | 1/1987 | Nielsen et al. | |
| 4,636,212 A | 1/1987 | Posin et al. | |
| 4,637,697 A | 1/1987 | Freeman | |
| 4,639,105 A | 1/1987 | Neefe | |
| 4,641,934 A | 2/1987 | Freeman | |
| 4,642,112 A | 2/1987 | Freeman | |
| 4,646,720 A | 3/1987 | Peyman | |
| 4,648,400 A | 3/1987 | Schneider et al. | |
| 4,655,774 A | 4/1987 | Choyce | |
| 4,662,370 A | 5/1987 | Hoffman et al. | |
| 4,665,913 A | 5/1987 | L'Esperance, Jr. | |
| 4,666,249 A | 5/1987 | Bauman et al. | |
| 4,666,446 A | 5/1987 | Koziol et al. | |
| 4,669,466 A | 6/1987 | L'Esperance, Jr. | |
| 4,669,834 A | 6/1987 | Richter | |
| 4,672,021 A | 6/1987 | Blumel et al. | |
| 4,674,503 A | 6/1987 | Peyman et al. | |
| 4,676,790 A | 6/1987 | Kern | |
| 4,676,791 A | 6/1987 | Le Master et al. | |
| 4,678,422 A | 7/1987 | York | |
| 4,685,921 A | 8/1987 | Peyman | |
| 4,685,922 A | 8/1987 | Peyman | |
| 4,701,038 A | 10/1987 | Neefe | |
| 4,702,574 A | 10/1987 | Bawa | |
| 4,702,865 A | 10/1987 | Koziol et al. | |
| 4,704,016 A | 11/1987 | de Carle | |
| 4,710,003 A | 12/1987 | Masuda et al. | |
| 4,713,446 A | 12/1987 | DeVore et al. | |
| 4,715,858 A | 12/1987 | Lindstrom | |
| 4,718,418 A | 1/1988 | L'Esperance | |
| 4,729,372 A | 3/1988 | L'Esperance, Jr. | |
| 4,729,373 A | 3/1988 | Peyman | |
| 4,732,148 A | 3/1988 | L'Esperance, Jr. | |
| 4,744,360 A | 5/1988 | Bath | |
| 4,753,654 A | 6/1988 | Posin et al. | |
| 4,767,647 A | 8/1988 | Bree | |
| 4,779,973 A | 10/1988 | Miller et al. | |
| 4,785,796 A | 11/1988 | Mattson | |
| 4,785,810 A | 11/1988 | Baccala et al. | |
| 4,787,903 A | 11/1988 | Grendahl | |
| 4,795,462 A | 1/1989 | Grendahl | |
| 4,796,623 A | 1/1989 | Krasner et al. | |
| 4,798,608 A | 1/1989 | Grendahl | |
| 4,799,478 A | 1/1989 | Fedorov et al. | |
| 4,799,784 A | 1/1989 | Safir | |
| 4,799,931 A | 1/1989 | Lindstrom | |
| 4,799,973 A | 1/1989 | Lindstrom | |
| 4,806,382 A | 2/1989 | Goldberg et al. | |
| 4,807,623 A | 2/1989 | Lieberman | |
| 4,808,181 A | 2/1989 | Kelman | |
| 4,813,955 A | 3/1989 | Achatz et al. | |
| 4,814,050 A | 3/1989 | McGraw et al. | |
| 4,817,789 A | 4/1989 | Paul | |
| 4,830,855 A | 5/1989 | Stewart | |
| 4,838,266 A | 6/1989 | Koziol et al. | |
| 4,840,175 A | 6/1989 | Peyman | |
| 4,842,599 A | 6/1989 | Bronstein | |
| 4,849,323 A | 7/1989 | Endo et al. | |
| 4,851,003 A | 7/1989 | Lindstrom | |
| 4,863,466 A | 9/1989 | Schlegel | |
| 4,865,601 A | 9/1989 | Caldwell et al. | |

(56) References Cited

U.S. PATENT DOCUMENTS

| | | |
|---|---|---|
| 4,869,587 A | 9/1989 | Breger |
| 4,878,910 A | 11/1989 | Koziol et al. |
| 4,881,860 A | 11/1989 | Kanazawa |
| 4,881,954 A | 11/1989 | Bikson et al. |
| 4,889,795 A | 12/1989 | Kaifu et al. |
| 4,890,913 A | 1/1990 | De Carle |
| 4,891,043 A | 1/1990 | Zeimer et al. |
| 4,892,543 A | 1/1990 | Turley |
| 4,898,461 A | 2/1990 | Portney |
| 4,903,695 A | 2/1990 | Warner et al. |
| 4,907,586 A | 3/1990 | Bille et al. |
| 4,923,297 A | 5/1990 | Arndt |
| 4,928,815 A | 5/1990 | Paul |
| 4,932,970 A | 6/1990 | Portney |
| 4,955,904 A | 9/1990 | Atebara et al. |
| 4,958,922 A | 9/1990 | Binh et al. |
| 4,959,070 A | 9/1990 | McDonald |
| 4,961,744 A | 10/1990 | Kilmer et al. |
| 4,965,545 A | 10/1990 | Johnson |
| 4,971,432 A | 11/1990 | Koeniger |
| 4,976,709 A | 12/1990 | Sand |
| 4,976,732 A | 12/1990 | Vorosmarthy |
| 4,983,181 A | 1/1991 | Civerchia |
| 4,985,559 A | 1/1991 | Goldberg et al. |
| 4,990,165 A | 2/1991 | Bikson et al. |
| 4,994,058 A | 2/1991 | Raven et al. |
| 4,994,080 A | 2/1991 | Shepard |
| 4,997,268 A | 3/1991 | Dauvergne |
| 5,002,571 A | 3/1991 | O'Donnel, Jr. |
| 5,013,319 A | 5/1991 | Davis |
| 5,019,097 A | 5/1991 | Knight et al. |
| 5,026,393 A | 6/1991 | Mackool |
| D318,117 S | 7/1991 | Michelson |
| 5,030,230 A | 7/1991 | White |
| 5,041,133 A | 8/1991 | Sayano et al. |
| 5,055,602 A | 10/1991 | Melpolder |
| 5,061,914 A | 10/1991 | Busch et al. |
| 5,063,942 A | 11/1991 | Kilmer et al. |
| 5,065,516 A | 11/1991 | Dulebohn |
| 5,067,961 A | 11/1991 | Kelman et al. |
| 5,076,684 A | 12/1991 | Simpson et al. |
| D323,891 S | 2/1992 | Arkel |
| 5,087,015 A | 2/1992 | Galley |
| 5,089,022 A | 2/1992 | Koester et al. |
| 5,089,024 A | 2/1992 | Christie et al. |
| 5,090,955 A | 2/1992 | Simon |
| 5,092,874 A | 3/1992 | Rogers |
| 5,094,521 A | 3/1992 | Jolson et al. |
| 5,098,443 A | 3/1992 | Parel et al. |
| 5,098,444 A | 3/1992 | Feaster |
| D325,500 S | 4/1992 | Dennis |
| 5,104,957 A | 4/1992 | Kelman et al. |
| 5,108,169 A | 4/1992 | Mandell |
| 5,108,427 A | 4/1992 | Majercik et al. |
| 5,108,428 A | 4/1992 | Capecchi et al. |
| 5,112,328 A | 5/1992 | Taboada et al. |
| 5,112,350 A | 5/1992 | Civerchia et al. |
| 5,116,111 A | 5/1992 | Simpson et al. |
| 5,119,555 A | 6/1992 | Johnson |
| 5,120,120 A | 6/1992 | Cohen |
| 5,120,121 A | 6/1992 | Rawlings et al. |
| 5,123,921 A | 6/1992 | Werblin et al. |
| 5,133,745 A | 7/1992 | Falcetta et al. |
| 5,139,518 A | 8/1992 | White |
| 5,149,331 A | 9/1992 | Ferdman et al. |
| 5,151,098 A | 9/1992 | Loertascher |
| 5,152,789 A | 10/1992 | Willis |
| 5,156,622 A | 10/1992 | Thompson |
| 5,158,572 A | 10/1992 | Nielsen |
| 5,160,463 A | 11/1992 | Evans et al. |
| 5,165,897 A | 11/1992 | Johnson |
| 5,166,712 A | 11/1992 | Portney |
| 5,171,318 A | 12/1992 | Gibson et al. |
| 5,172,143 A | 12/1992 | Baude et al. |
| 5,185,152 A | 2/1993 | Peyman |
| 5,188,125 A | 2/1993 | Kilmer et al. |
| 5,188,494 A | 2/1993 | Hatin |
| 5,192,316 A | 3/1993 | Ting |
| 5,192,318 A | 3/1993 | Schneider et al. |
| 5,196,026 A | 3/1993 | Barrett et al. |
| 5,196,027 A | 3/1993 | Thompson et al. |
| 5,201,762 A | 4/1993 | Hauber |
| 5,203,865 A | 4/1993 | Siepser |
| 5,215,104 A | 6/1993 | Steinert |
| 5,219,844 A | 6/1993 | Peyman et al. |
| 5,225,858 A | 7/1993 | Portney |
| 5,239,066 A | 8/1993 | Falkow et al. |
| 5,245,367 A | 9/1993 | Miller et al. |
| 5,245,738 A | 9/1993 | Johnson |
| 5,258,412 A | 11/1993 | Peyman et al. |
| 5,260,727 A | 11/1993 | Oksman et al. |
| 5,261,997 A | 11/1993 | Inselmann |
| 5,269,795 A | 12/1993 | Arnott |
| 5,269,812 A | 12/1993 | White |
| 5,270,744 A | 12/1993 | Portney |
| 5,274,404 A | 12/1993 | Michael |
| 5,282,971 A | 2/1994 | Degen et al. |
| 5,288,293 A | 2/1994 | O'Donnel, Jr. |
| 5,288,436 A | 2/1994 | Liu et al. |
| 5,290,301 A | 3/1994 | Lieberman |
| 5,292,514 A | 3/1994 | Capecchi et al. |
| 5,296,305 A | 3/1994 | Baude et al. |
| 5,296,881 A | 3/1994 | Freeman |
| D345,796 S | 4/1994 | Pernicka |
| 5,300,116 A | 4/1994 | Chirila et al. |
| 5,300,118 A | 4/1994 | Silvestrini et al. |
| 5,302,978 A | 4/1994 | Evans et al. |
| 5,306,297 A | 4/1994 | Rheinish et al. |
| 5,310,654 A | 5/1994 | Isberg et al. |
| 5,312,330 A | 5/1994 | Klopotek |
| 5,312,393 A | 5/1994 | Mastel |
| 5,312,424 A | 5/1994 | Kilmer et al. |
| 5,314,439 A | 5/1994 | Sugita |
| 5,314,961 A | 5/1994 | Anton et al. |
| 5,315,344 A | 5/1994 | Clark et al. |
| 5,318,044 A | 6/1994 | Kilmer et al. |
| 5,318,046 A | 6/1994 | Rozakis |
| 5,318,047 A | 6/1994 | Davenport et al. |
| 5,322,649 A | 6/1994 | Rheinish et al. |
| 5,323,788 A | 6/1994 | Silvestrini et al. |
| 5,325,880 A | 7/1994 | Johnson et al. |
| 5,332,802 A | 7/1994 | Kelman et al. |
| 5,336,261 A | 8/1994 | Barret et al. |
| 5,346,689 A | 9/1994 | Peyman et al. |
| 5,354,331 A | 10/1994 | Scharcar |
| 5,358,520 A | 10/1994 | Patel |
| 5,366,499 A | 11/1994 | Py |
| 5,368,604 A | 11/1994 | Kilmer et al. |
| 5,372,580 A | 12/1994 | Simon et al. |
| 5,374,272 A | 12/1994 | Arpa et al. |
| D354,566 S | 1/1995 | Donahoo |
| 5,391,201 A | 2/1995 | Barret et al. |
| 5,401,508 A | 3/1995 | Manesis |
| 5,403,335 A | 4/1995 | Loomas et al. |
| 5,405,384 A | 4/1995 | Silvestrini |
| 5,414,477 A | 5/1995 | Jahnke |
| 5,422,424 A | 6/1995 | Selsted et al. |
| 5,433,745 A | 7/1995 | Graham et al. |
| 5,434,630 A | 7/1995 | Bransome |
| 5,437,274 A | 8/1995 | Khoobehi et al. |
| 5,441,511 A | 8/1995 | Hanna |
| 5,458,819 A | 10/1995 | Chirila et al. |
| 5,466,260 A | 11/1995 | Silvestrini et al. |
| 5,474,548 A | 12/1995 | Knopp et al. |
| 5,475,452 A | 12/1995 | Kuhn et al. |
| 5,476,515 A | 12/1995 | Kelman et al. |
| 5,480,427 A | 1/1996 | Kelman et al. |
| 5,489,300 A | 2/1996 | Capecchi et al. |
| 5,496,339 A | 3/1996 | Koepnick |
| 5,505,722 A | 4/1996 | Kilmer et al. |
| 5,505,723 A | 4/1996 | Muller |
| 5,507,740 A | 4/1996 | O'Donnel, Jr. |
| 5,507,741 A | 4/1996 | L'Esperance, Jr. |
| 5,507,759 A | 4/1996 | Nordan |

(56) References Cited

U.S. PATENT DOCUMENTS

| | | |
|---|---|---|
| 5,509,922 A | 4/1996 | Aranyi et al. |
| 5,516,467 A | 5/1996 | Niwa et al. |
| 5,516,522 A | 5/1996 | Peyman et al. |
| 5,522,888 A | 6/1996 | Civerchia |
| 5,526,178 A | 6/1996 | Goldstein et al. |
| 5,527,356 A | 6/1996 | Peyman et al. |
| 5,527,524 A | 7/1996 | Tomalla et al. |
| 5,547,468 A | 8/1996 | Simon et al. |
| 5,547,473 A | 8/1996 | Peyman |
| 5,567,365 A | 10/1996 | Weinschenk, III et al. |
| D375,245 S | 11/1996 | Irving |
| 5,571,177 A | 11/1996 | Deacon et al. |
| 5,579,063 A | 11/1996 | Magnante et al. |
| RE35,421 E | 1/1997 | Ruiz et al. |
| 5,591,185 A | 1/1997 | Kilmer et al. |
| 5,592,246 A | 1/1997 | Kuhn et al. |
| 5,599,341 A | 2/1997 | Mathis et al. |
| 5,599,537 A | 2/1997 | Miller, III et al. |
| 5,605,938 A | 2/1997 | Roufa et al. |
| 5,607,437 A | 3/1997 | Simon et al. |
| 5,607,472 A | 3/1997 | Thompson |
| 5,608,471 A | 3/1997 | Miller |
| 5,610,719 A | 3/1997 | Allen et al. |
| 5,624,456 A | 4/1997 | Hellenkamp |
| 5,627,613 A | 5/1997 | Kaneko |
| 5,628,794 A | 5/1997 | Lindstrom |
| 5,628,795 A | 5/1997 | Langerman |
| 5,628,798 A | 5/1997 | Eggleston et al. |
| 5,631,243 A | 5/1997 | Kelman et al. |
| 5,632,773 A | 5/1997 | Graham et al. |
| 5,643,249 A | 7/1997 | Amano et al. |
| 5,645,582 A | 7/1997 | Silvestrini et al. |
| 5,647,865 A | 7/1997 | Swinger |
| 5,653,752 A | 8/1997 | Silvestrini et al. |
| 5,662,706 A | 9/1997 | Legerton et al. |
| 5,662,908 A | 9/1997 | Falkow et al. |
| 5,672,885 A | 9/1997 | Allen et al. |
| 5,674,724 A | 10/1997 | Miller, III et al. |
| 5,674,736 A | 10/1997 | Miller, III et al. |
| 5,693,092 A | 12/1997 | Silvestrini et al. |
| 5,695,983 A | 12/1997 | Miller et al. |
| 5,697,923 A | 12/1997 | Poler |
| 5,697,973 A | 12/1997 | Peyman et al. |
| 5,702,440 A | 12/1997 | Portney |
| 5,708,049 A | 1/1998 | Katagiri et al. |
| 5,713,844 A | 2/1998 | Peyman |
| 5,713,957 A | 2/1998 | Steele et al. |
| 5,719,656 A | 2/1998 | Bowling |
| 5,720,894 A | 2/1998 | Neev et al. |
| 5,722,971 A | 3/1998 | Peyman |
| 5,725,575 A | 3/1998 | O'Donnel, Jr. |
| 5,731,196 A | 3/1998 | Miller, III et al. |
| 5,731,862 A | 3/1998 | Winkler |
| 5,733,334 A | 3/1998 | Lee et al. |
| 5,733,760 A | 3/1998 | Lu et al. |
| 5,746,558 A | 5/1998 | Nygren et al. |
| 5,752,960 A | 5/1998 | Nallakrishnan |
| 5,752,967 A | 5/1998 | Kritzinger et al. |
| 5,757,458 A | 5/1998 | Miller et al. |
| 5,766,171 A | 6/1998 | Silvestrini |
| 5,769,889 A | 6/1998 | Kelman |
| 5,771,088 A | 6/1998 | Perrott |
| 5,771,742 A | 6/1998 | Bokaie et al. |
| 5,774,202 A | 6/1998 | Abraham et al. |
| 5,782,911 A | 7/1998 | Herrick |
| 5,785,651 A | 7/1998 | Kuhn et al. |
| 5,786,883 A | 7/1998 | Miller et al. |
| 5,800,533 A | 9/1998 | Eggleston et al. |
| 5,806,530 A | 9/1998 | Herrick |
| 5,814,680 A | 9/1998 | Imafuku et al. |
| 5,824,086 A | 10/1998 | Silvestrini |
| 5,833,701 A | 11/1998 | Gordon |
| 5,836,313 A | 11/1998 | Perez et al. |
| 5,840,848 A | 11/1998 | Sturrock et al. |
| 5,843,105 A | 12/1998 | Mathis et al. |
| 5,843,186 A | 12/1998 | Upsher |
| 5,846,256 A | 12/1998 | Mathis et al. |
| 5,855,605 A | 1/1999 | Herrick |
| 5,858,980 A | 1/1999 | Weiner et al. |
| 5,861,486 A | 1/1999 | DeVore et al. |
| 5,863,537 A | 1/1999 | Dalliet et al. |
| 5,864,128 A | 1/1999 | Plesko |
| 5,864,378 A | 1/1999 | Portney |
| 5,865,729 A | 2/1999 | Meehan et al. |
| 5,870,167 A | 2/1999 | Knopp et al. |
| 5,874,537 A | 2/1999 | Kelman et al. |
| 5,876,442 A | 3/1999 | Lipshitz et al. |
| 5,888,243 A | 3/1999 | Silverstrini |
| 5,903,099 A | 5/1999 | Johnson et al. |
| 5,905,561 A | 5/1999 | Lee et al. |
| 5,919,185 A | 7/1999 | Peyman |
| 5,928,283 A | 7/1999 | Gross et al. |
| 5,929,968 A | 7/1999 | Cotie et al. |
| 5,935,140 A | 8/1999 | Buratto |
| 5,944,752 A | 8/1999 | Silvestrini |
| 5,960,812 A | 10/1999 | Johnson |
| 5,964,748 A | 10/1999 | Peyman |
| 5,964,776 A | 10/1999 | Peyman |
| 5,965,330 A | 10/1999 | Evans et al. |
| 5,968,062 A | 10/1999 | Thomas et al. |
| 5,980,040 A | 11/1999 | Xu et al. |
| 5,997,559 A | 12/1999 | Ziemer |
| 6,001,386 A | 12/1999 | Ashton et al. |
| 6,010,510 A | 1/2000 | Brown et al. |
| 6,010,901 A | 1/2000 | Miller, III et al. |
| 6,017,121 A | 1/2000 | Chateau et al. |
| 6,024,447 A | 2/2000 | Portney |
| 6,036,957 A | 3/2000 | Weiner et al. |
| D423,669 S | 4/2000 | Huttner |
| 6,050,999 A | 4/2000 | Paraschac et al. |
| 6,051,023 A | 4/2000 | Kilmer et al. |
| 6,063,073 A | 5/2000 | Peyman |
| 6,066,171 A | 5/2000 | Lipshitz et al. |
| 6,083,236 A | 7/2000 | Feingold |
| 6,086,204 A | 7/2000 | Magnante |
| 6,090,141 A | 7/2000 | Lindstrom |
| 6,096,077 A | 8/2000 | Callahan et al. |
| 6,102,946 A | 8/2000 | Nigam |
| 6,106,552 A | 8/2000 | Lacombe et al. |
| 6,110,166 A | 8/2000 | Juhasz |
| 6,125,294 A | 9/2000 | Scholl et al. |
| 6,126,286 A | 10/2000 | Portney |
| 6,138,307 A | 10/2000 | McDonald |
| 6,143,010 A | 11/2000 | Silvestrini |
| 6,152,959 A | 11/2000 | Portney |
| 6,161,544 A | 12/2000 | DeVore et al. |
| 6,164,282 A | 12/2000 | Gwon et al. |
| 6,165,189 A | 12/2000 | Ziemer |
| 6,171,336 B1 | 1/2001 | Sawusch |
| 6,175,754 B1 | 1/2001 | Scholl et al. |
| 6,176,878 B1 | 1/2001 | Gwon et al. |
| 6,178,593 B1 | 1/2001 | Carlson |
| 6,183,498 B1 | 2/2001 | DeVore et al. |
| D439,338 S | 3/2001 | Huttner |
| 6,197,019 B1 | 3/2001 | Peyman |
| 6,197,057 B1 | 3/2001 | Peyman et al. |
| 6,197,934 B1 | 3/2001 | DeVore et al. |
| 6,203,538 B1 | 3/2001 | Peyman |
| 6,204,365 B1 | 3/2001 | DeVore et al. |
| 6,210,005 B1 | 4/2001 | Portney |
| 6,210,401 B1 | 4/2001 | Lai |
| 6,214,044 B1 | 4/2001 | Silvestrini |
| 6,217,571 B1 | 4/2001 | Peyman |
| 6,217,596 B1 | 4/2001 | Farah |
| 6,218,360 B1 | 4/2001 | Cintron et al. |
| 6,221,067 B1 | 4/2001 | Peyman |
| 6,221,105 B1 | 4/2001 | Portney |
| 6,228,113 B1 | 5/2001 | Kauffman |
| 6,228,114 B1 | 5/2001 | Lee |
| 6,228,115 B1 | 5/2001 | Hoffmann et al. |
| 6,231,582 B1 | 5/2001 | Gandianco et al. |
| 6,251,118 B1 | 6/2001 | Proudfoot et al. |
| 6,264,648 B1 | 7/2001 | Peyman |
| D447,237 S | 8/2001 | Huttner et al. |

(56) References Cited

U.S. PATENT DOCUMENTS

| | | |
|---|---|---|
| 6,277,146 B1 | 8/2001 | Peyman et al. |
| 6,280,449 B1 | 8/2001 | Blake |
| 6,280,470 B1 | 8/2001 | Peyman |
| 6,280,471 B1 | 8/2001 | Peyman |
| 6,283,595 B1 | 9/2001 | Breger |
| 6,302,877 B1 | 10/2001 | Ruiz |
| 6,308,590 B1 | 10/2001 | Berto |
| 6,312,424 B1 | 11/2001 | Largent |
| 6,316,153 B1 | 11/2001 | Goodman et al. |
| 6,335,006 B1 | 1/2002 | Miller |
| 6,357,875 B1 | 3/2002 | Herrick |
| 6,358,280 B1 | 3/2002 | Herrick |
| 6,361,560 B1 | 3/2002 | Nigam |
| 6,371,973 B1 | 4/2002 | Tepper |
| 6,376,153 B2 | 4/2002 | Uchikawa et al. |
| 6,387,379 B1 | 5/2002 | Goldberg et al. |
| 6,391,055 B1 | 5/2002 | Ikada et al. |
| 6,399,734 B1 | 6/2002 | Hodd et al. |
| 6,403,947 B1 | 6/2002 | Hoyt et al. |
| 6,406,494 B1 | 6/2002 | Laguette et al. |
| 6,413,276 B1 | 7/2002 | Werblin |
| 6,416,179 B1 | 7/2002 | Lieberman et al. |
| 6,419,697 B1 | 7/2002 | Kelman |
| 6,423,093 B1 | 7/2002 | Hicks et al. |
| 6,425,917 B1 | 7/2002 | Blake |
| 6,432,246 B1 | 8/2002 | Blake |
| 6,436,092 B1 | 8/2002 | Peyman |
| 6,450,642 B1 | 9/2002 | Jethmalani et al. |
| 6,454,800 B2 | 9/2002 | Dalton et al. |
| 6,457,826 B1 | 10/2002 | Lett |
| 6,458,141 B1 | 10/2002 | Peyman |
| 6,470,108 B1 | 10/2002 | Johnson |
| 6,488,707 B1 | 12/2002 | Callahan et al. |
| 6,494,910 B1 | 12/2002 | Ganem et al. |
| 6,497,700 B1 | 12/2002 | LaHaye |
| 6,503,276 B2 | 1/2003 | Lang et al. |
| 6,515,006 B2 | 2/2003 | Horn |
| 6,520,955 B2 | 2/2003 | Reynard |
| 6,527,389 B2 | 3/2003 | Portney |
| 6,533,905 B2 | 3/2003 | Johnson et al. |
| 6,536,899 B1 | 3/2003 | Fiala |
| 6,551,307 B2 | 4/2003 | Peyman |
| 6,554,424 B1 | 4/2003 | Miller et al. |
| 6,554,860 B2 | 4/2003 | Hoffmann et al. |
| 6,555,103 B2 | 4/2003 | Leukel et al. |
| 6,569,199 B1 | 5/2003 | Dotan et al. |
| 6,575,573 B2 | 6/2003 | Lai et al. |
| 6,581,993 B2 | 6/2003 | Nigam |
| RE38,193 E | 7/2003 | Bowling |
| 6,588,022 B1 | 7/2003 | Anders et al. |
| 6,588,902 B2 | 7/2003 | Isogai |
| 6,589,280 B1 | 7/2003 | Koziol |
| 6,592,621 B1 | 7/2003 | Domino |
| 6,596,026 B1 | 7/2003 | Gross et al. |
| 6,599,305 B1 | 7/2003 | Feingold |
| 6,607,527 B1 | 8/2003 | Ruiz et al. |
| 6,607,556 B1 | 8/2003 | Nigam |
| 6,613,088 B1 | 9/2003 | Babizhayev |
| 6,614,570 B2 | 9/2003 | Johnson et al. |
| 6,620,634 B2 | 9/2003 | Johnson et al. |
| 6,623,497 B1 | 9/2003 | Feingold |
| 6,623,522 B2 | 9/2003 | Nigam |
| 6,624,730 B2 | 9/2003 | Johnson et al. |
| 6,626,914 B2 | 9/2003 | Nigam |
| 6,626,941 B2 | 9/2003 | Nigam |
| 6,632,244 B1 | 10/2003 | Nigam |
| 6,638,304 B2 | 10/2003 | Azar |
| 6,663,668 B1 | 12/2003 | Chaouk et al. |
| 6,669,795 B2 | 12/2003 | Johnson et al. |
| 6,673,112 B2 | 1/2004 | Nigam |
| 6,692,126 B1 | 2/2004 | Xie et al. |
| 6,702,807 B2 | 3/2004 | Peyman |
| 6,729,599 B2 | 5/2004 | Johnson |
| 6,740,116 B2 | 5/2004 | Morcher |
| 6,742,761 B2 | 6/2004 | Johnson et al. |
| 6,746,890 B2 | 6/2004 | Gupta et al. |
| 6,749,632 B2 | 6/2004 | Jethmalani et al. |
| 6,755,819 B1 | 6/2004 | Waelti |
| 6,755,858 B1 | 6/2004 | White |
| D493,889 S | 8/2004 | Yoo |
| 6,786,926 B2 | 9/2004 | Peyman |
| 6,790,298 B2 | 9/2004 | Johnson et al. |
| 6,811,256 B1 | 11/2004 | Becherer et al. |
| 6,813,097 B2 | 11/2004 | Jethmalani et al. |
| 6,824,266 B2 | 11/2004 | Jethmalani et al. |
| 6,849,090 B2 | 2/2005 | Nigam |
| 6,851,804 B2 | 2/2005 | Jethmalani et al. |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,951,556 B2 | 10/2005 | Epstein |
| 6,966,648 B2 | 11/2005 | Miller et al. |
| 6,976,997 B2 | 12/2005 | Noolandi et al. |
| 6,986,763 B2 | 1/2006 | Holmen |
| 6,989,008 B2 | 1/2006 | Peyman |
| 7,001,374 B2 | 2/2006 | Peyman |
| 7,008,447 B2 | 3/2006 | Koziol |
| 7,025,455 B2 | 4/2006 | Roffman |
| 7,097,649 B2 | 8/2006 | Meyer |
| 7,179,292 B2 | 2/2007 | Worst et al. |
| 7,207,998 B2 | 4/2007 | Feingold |
| 7,364,674 B1 | 4/2008 | Hoover |
| D569,512 S | 5/2008 | Poll et al. |
| D571,915 S | 6/2008 | Poll et al. |
| 7,399,811 B2 | 7/2008 | Mentak et al. |
| 7,404,637 B2 | 7/2008 | Miller et al. |
| 7,404,638 B2 | 7/2008 | Miller et al. |
| 7,446,157 B2 | 11/2008 | Mentak et al. |
| 7,462,194 B1 | 12/2008 | Blake |
| 7,491,350 B2 | 2/2009 | Silvestrini |
| D589,615 S | 3/2009 | Doenges |
| 7,628,810 B2 | 12/2009 | Christie et al. |
| 7,645,291 B2 | 1/2010 | Ross et al. |
| 7,645,299 B2 | 1/2010 | Koziol |
| 7,745,555 B2 | 6/2010 | Mentak et al. |
| 7,828,844 B2 | 11/2010 | Marmo et al. |
| 7,976,577 B2 | 7/2011 | Silvestrini |
| D645,337 S | 9/2011 | Hsu et al. |
| 8,048,972 B2 | 11/2011 | Mentak et al. |
| 8,079,706 B2 | 12/2011 | Silvestrini et al. |
| D656,256 S | 3/2012 | Christie et al. |
| 8,216,765 B2 | 7/2012 | Morimitsu et al. |
| 8,287,592 B2 | 10/2012 | Silvestrini |
| 8,343,215 B2 | 1/2013 | Miller et al. |
| 8,349,006 B2 | 1/2013 | Zhao et al. |
| D681,086 S | 4/2013 | Christie et al. |
| 8,420,753 B2 | 4/2013 | Mentak et al. |
| 8,460,374 B2 | 6/2013 | Christie et al. |
| 8,568,478 B2 | 10/2013 | Zickler et al. |
| 8,604,098 B2 | 12/2013 | Boydston et al. |
| 8,633,292 B2 | 1/2014 | Hu et al. |
| 8,740,978 B2 | 6/2014 | Weeber et al. |
| 8,752,958 B2 | 6/2014 | Miller et al. |
| 9,204,962 B2 | 12/2015 | Silvestrini |
| 9,603,704 B2 | 3/2017 | Silvestrini |
| 2001/0004702 A1 | 6/2001 | Peyman |
| 2001/0027314 A1 | 10/2001 | Peyman |
| 2001/0034516 A1 | 10/2001 | Peyman |
| 2001/0047203 A1 | 11/2001 | Dalton et al. |
| 2001/0050750 A1 | 12/2001 | Breger |
| 2002/0010510 A1 | 1/2002 | Silverstrini |
| 2002/0016629 A1 | 2/2002 | Sandstedt et al. |
| 2002/0028330 A1 | 3/2002 | Patel et al. |
| 2002/0029981 A1 | 3/2002 | Nigam |
| 2002/0042004 A1 | 4/2002 | Sandstedt et al. |
| 2002/0055753 A1 | 5/2002 | Silverstrini |
| 2002/0057148 A1 | 5/2002 | Johnson et al. |
| 2002/0075447 A1 | 6/2002 | Andino et al. |
| 2002/0082288 A1 | 6/2002 | Horn |
| 2002/0107337 A1 | 8/2002 | Rosenzweig et al. |
| 2002/0107566 A1 | 8/2002 | Nigam |
| 2002/0111677 A1 | 8/2002 | Nigam |
| 2002/0120329 A1 | 8/2002 | Lang et al. |

(56) References Cited

U.S. PATENT DOCUMENTS

| | | |
|---|---|---|
| 2002/0128710 A1 | 9/2002 | Eggleston |
| 2002/0133228 A1 | 9/2002 | Sarver |
| 2002/0138070 A1 | 9/2002 | Peyman |
| 2002/0167640 A1 | 11/2002 | Francis et al. |
| 2002/0167735 A1 | 11/2002 | Jethmalani et al. |
| 2002/0169491 A1 | 11/2002 | Foster et al. |
| 2002/0169505 A1 | 11/2002 | Jethmalani et al. |
| 2002/0173846 A1 | 11/2002 | Blake et al. |
| 2002/0187986 A1 | 12/2002 | Horn |
| 2002/0188351 A1 | 12/2002 | Laguette |
| 2002/0196409 A1 | 12/2002 | Jani |
| 2003/0002994 A1 | 1/2003 | Johnson et al. |
| 2003/0007122 A1 | 1/2003 | Streibig |
| 2003/0014021 A1 | 1/2003 | Holmen |
| 2003/0014042 A1 | 1/2003 | Juhasz et al. |
| 2003/0014107 A1 | 1/2003 | Reynard |
| 2003/0033013 A1 | 2/2003 | Callahan et al. |
| 2003/0045930 A1 | 3/2003 | Nguyen |
| 2003/0048411 A1 | 3/2003 | Jethmalani et al. |
| 2003/0055497 A1 | 3/2003 | Hicks et al. |
| 2003/0071893 A1 | 4/2003 | Miller et al. |
| 2003/0078655 A1 | 4/2003 | Callahan et al. |
| 2003/0088313 A1 | 5/2003 | Nigam |
| 2003/0090013 A1 | 5/2003 | Jethmalani et al. |
| 2003/0090624 A1 | 5/2003 | Jethmalani et al. |
| 2003/0093083 A1 | 5/2003 | Peyman |
| 2003/0093150 A1 | 5/2003 | Jethmalani et al. |
| 2003/0105521 A1 | 6/2003 | Perez |
| 2003/0115718 A1 | 6/2003 | Bechthold |
| 2003/0127318 A1 | 7/2003 | Johnson et al. |
| 2003/0128336 A1 | 7/2003 | Jethmalani et al. |
| 2003/0151825 A1 | 8/2003 | Bielawski et al. |
| 2003/0151831 A1 | 8/2003 | Sandstedt et al. |
| 2003/0174375 A1 | 9/2003 | Jethmalani et al. |
| 2003/0176521 A1 | 9/2003 | Jethmalani et al. |
| 2003/0216763 A1 | 11/2003 | Patel |
| 2003/0220653 A1 | 11/2003 | Perez |
| 2004/0014253 A1 | 1/2004 | Gupta et al. |
| 2004/0015234 A1 | 1/2004 | Peyman |
| 2004/0019379 A1 | 1/2004 | Glick et al. |
| 2004/0047014 A1 | 3/2004 | Parker et al. |
| 2004/0049174 A1 | 3/2004 | Peyman |
| 2004/0056371 A1 | 3/2004 | Liao et al. |
| 2004/0068317 A1 | 4/2004 | Knight |
| 2004/0078075 A1 | 4/2004 | Koziol |
| 2004/0080239 A1 | 4/2004 | Gupta et al. |
| 2004/0086479 A1 | 5/2004 | Grinstaff et al. |
| 2004/0106929 A1 | 6/2004 | Masket |
| 2004/0243231 A1 | 12/2004 | Koziol |
| 2005/0027354 A1 | 2/2005 | Brady et al. |
| 2005/0027355 A1 | 2/2005 | Murakami |
| 2005/0031697 A1 | 2/2005 | Vehige et al. |
| 2005/0033420 A1 | 2/2005 | Christie et al. |
| 2005/0046794 A1 | 3/2005 | Silvestrini et al. |
| 2005/0049621 A1 | 3/2005 | Feingold et al. |
| 2005/0080485 A1 | 4/2005 | Nigam |
| 2005/0090895 A1 | 4/2005 | Peyman |
| 2005/0099597 A1 | 5/2005 | Sandstedt et al. |
| 2005/0119738 A1 | 6/2005 | Nigam |
| 2005/0124983 A1 | 6/2005 | Fret et al. |
| 2005/0143717 A1 | 6/2005 | Peyman |
| 2005/0143812 A1 | 6/2005 | Paul et al. |
| 2005/0182488 A1 | 8/2005 | Peyman |
| 2005/0187621 A1 | 8/2005 | Brady |
| 2005/0222679 A1 | 10/2005 | Peyman |
| 2005/0228376 A1 | 10/2005 | Boomer et al. |
| 2005/0246015 A1 | 11/2005 | Miller |
| 2005/0246016 A1 | 11/2005 | Miller et al. |
| 2005/0246019 A1 | 11/2005 | Blake et al. |
| 2006/0064077 A1 | 3/2006 | Peyman |
| 2006/0079959 A1 | 4/2006 | Christie et al. |
| 2006/0079960 A1 | 4/2006 | Christie et al. |
| 2006/0095127 A1 | 5/2006 | Feingold et al. |
| 2006/0098162 A1 | 5/2006 | Bandhauer et al. |
| 2006/0113054 A1 | 6/2006 | Silvestrini |
| 2006/0118263 A1 | 6/2006 | Silvestrini |
| 2006/0184243 A1 | 8/2006 | Yilmaz |
| 2006/0203192 A1 | 9/2006 | Miller et al. |
| 2006/0235428 A1 | 10/2006 | Silvestrini |
| 2006/0241751 A1 | 10/2006 | Marmo et al. |
| 2006/0252844 A1 | 11/2006 | Mentak |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271027 A1 | 11/2006 | Silvestrini et al. |
| 2006/0271176 A1 | 11/2006 | Christie et al. |
| 2006/0271177 A1 | 11/2006 | Christie et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0016234 A1 | 1/2007 | Daxer |
| 2007/0129797 A1 | 6/2007 | Lang et al. |
| 2007/0219542 A1 | 9/2007 | Yahagi |
| 2007/0225691 A1 | 9/2007 | Silvestrini et al. |
| 2008/0033546 A1 | 2/2008 | Liang |
| 2008/0077238 A1 | 3/2008 | Deacon et al. |
| 2008/0125862 A1 | 5/2008 | Blake |
| 2008/0151183 A1 | 6/2008 | Altmann |
| 2008/0212030 A1 | 9/2008 | Bentley et al. |
| 2008/0275462 A1 | 11/2008 | Feingold |
| 2009/0012505 A1 | 1/2009 | Chernyak |
| 2009/0059168 A1 | 3/2009 | Miller et al. |
| 2009/0069817 A1 | 3/2009 | Peyman |
| 2009/0204207 A1 | 8/2009 | Blum et al. |
| 2009/0222086 A1 | 9/2009 | Lui et al. |
| 2009/0287306 A1 | 11/2009 | Smith et al. |
| 2009/0306773 A1 | 12/2009 | Silvestrini et al. |
| 2010/0149618 A1 | 6/2010 | Sprague |
| 2010/0234942 A1 | 9/2010 | Peyman |
| 2010/0312336 A1 | 12/2010 | Hong et al. |
| 2011/0040376 A1 | 2/2011 | Christie et al. |
| 2011/0172675 A1 | 7/2011 | Danta et al. |
| 2011/0245818 A1 | 10/2011 | Weinschenk, III |
| 2011/0245919 A1 | 10/2011 | Pettit |
| 2012/0143325 A1 | 6/2012 | Christie et al. |
| 2012/0203239 A1 | 8/2012 | Vukich et al. |
| 2012/0245683 A1 | 9/2012 | Christie et al. |
| 2012/0309761 A1 | 12/2012 | Chow et al. |
| 2012/0310338 A1 | 12/2012 | Christie et al. |
| 2013/0053953 A1 | 2/2013 | Silvestrini |
| 2013/0103147 A1 | 4/2013 | Christie et al. |
| 2013/0131795 A1 | 5/2013 | Miller et al. |
| 2013/0238091 A1 | 9/2013 | Danta et al. |
| 2013/0268071 A1 | 10/2013 | Vilupuru et al. |
| 2014/0131905 A1 | 5/2014 | Webb |

FOREIGN PATENT DOCUMENTS

| | | |
|---|---|---|
| AR | 244 890 | 11/1993 |
| AU | 739297 | 1/2002 |
| AU | 0772492 | 8/2004 |
| AU | 778310 | 3/2005 |
| AU | 2003252004 | 3/2010 |
| AU | 2006236715 | 6/2012 |
| BR | 0008601 A | 12/2001 |
| BR | 0008624 A | 12/2001 |
| BR | PI-9809289-8 | 12/2006 |
| CA | 2286718 | 11/2008 |
| CN | 1253484 A | 5/2000 |
| CN | 1875895 | 12/2006 |
| CN | 101198294 | 6/2008 |
| CN | 101198364 | 6/2008 |
| CN | 101322663 | 12/2008 |

(56) References Cited

FOREIGN PATENT DOCUMENTS

| | | |
|---|---|---|
| CN | 102448404 | 5/2012 |
| CN | 102470033 A | 5/2012 |
| DE | 3433581 | 3/1986 |
| DE | 41 34 320 A1 | 4/1992 |
| EP | 0165652 | 12/1985 |
| EP | 0225098 | 6/1987 |
| EP | 0286433 | 10/1988 |
| EP | 0443094 A2 | 8/1991 |
| EP | 0457553 A2 | 11/1991 |
| EP | 0941717 | 9/1999 |
| EP | 1014872 | 7/2000 |
| EP | 1173790 | 1/2002 |
| EP | 1267998 | 1/2003 |
| EP | 1381326 | 1/2004 |
| EP | 1871298 | 4/2006 |
| EP | 1159033 | 1/2007 |
| EP | 1827330 | 9/2007 |
| EP | 1845896 | 10/2007 |
| EP | 1890736 | 2/2008 |
| EP | 1158936 | 7/2008 |
| EP | 1997530 | 12/2008 |
| EP | 1534188 | 9/2010 |
| EP | 2258311 | 12/2010 |
| EP | 2301477 | 3/2011 |
| EP | 1635739 | 9/2011 |
| EP | 2464310 | 6/2012 |
| EP | 2464311 | 6/2012 |
| EP | 2506803 | 10/2012 |
| EP | 2967839 | 1/2016 |
| FR | 369 993 | 1/1907 |
| FR | 1115140 | 12/1955 |
| FR | 1400566 | 4/1965 |
| FR | 2599156 | 5/1986 |
| FR | 2620687 | 3/1989 |
| FR | 2649605 | 1/1991 |
| FR | 2790944 | 9/2000 |
| GB | 1 026 839 | 4/1966 |
| GB | 1276003 | 6/1972 |
| GB | 1 547 525 | 6/1979 |
| GB | 2242835 | 10/1991 |
| HK | 1028531 | 2/2011 |
| HK | 1151451 | 2/2012 |
| HK | 11553484 | 5/2012 |
| HK | 1166457 A | 11/2012 |
| HK | 1169935 A | 2/2013 |
| JP | 62167343 A | 7/1987 |
| JP | 63-17096 | 4/1988 |
| JP | 64-002644 | 1/1989 |
| JP | 1990-7954 | 1/1990 |
| JP | 03-001857 | 1/1991 |
| JP | 04-158859 | 6/1992 |
| JP | 04-223425 | 8/1992 |
| JP | 06-509731 | 3/1993 |
| JP | H05-65340 | 9/1993 |
| JP | 6-502782 | 3/1994 |
| JP | 6-509731 | 11/1994 |
| JP | 07-050242 | 2/1995 |
| JP | 07-178125 | 7/1995 |
| JP | 07-265340 | 10/1995 |
| JP | 08-103457 | 4/1996 |
| JP | 09-502542 | 3/1997 |
| JP | 11-503657 | 8/1997 |
| JP | 2002-14772 | 1/2002 |
| JP | 2003-527228 | 9/2003 |
| JP | 2004-510199 | 4/2004 |
| JP | 2004-538034 | 12/2004 |
| JP | 2005-533576 | 11/2005 |
| JP | 2007-516019 | 6/2007 |
| JP | 2007-523720 | 8/2007 |
| JP | 4114036 | 4/2008 |
| JP | 2008-517671 | 5/2008 |
| JP | 2008-536574 | 9/2008 |
| JP | 2008-536576 | 9/2008 |
| JP | 4182390 | 9/2008 |
| JP | 2010-227615 | 10/2010 |
| JP | 2010-126600 | 2/2011 |
| JP | 4676761 | 2/2011 |
| JP | 4689615 | 2/2011 |
| JP | 4746052 | 5/2011 |
| KR | 10-0335722 | 5/2002 |
| KR | 600210 | 7/2006 |
| MX | 1008759 A | 7/2003 |
| MX | 226369 | 2/2005 |
| MX | 227913 | 3/2006 |
| NZ | 562987 | 2/2010 |
| RU | 2138837 C1 | 9/1999 |
| SG | 68726 | 2/2002 |
| SG | 83306 | 2/2004 |
| SG | 83307 | 7/2004 |
| SG | 200716909-7 | 3/2011 |
| SU | 1380743 A1 | 3/1998 |
| WO | WO 87/05797 | 10/1987 |
| WO | WO 87/07165 | 12/1987 |
| WO | WO 91/16865 | 11/1991 |
| WO | WO 92/05694 | 4/1992 |
| WO | WO 93/03776 | 3/1993 |
| WO | WO 93/08878 | 5/1993 |
| WO | WO 93/12735 | 7/1993 |
| WO | WO 93/20763 | 10/1993 |
| WO | WO 94/01058 | 1/1994 |
| WO | WO 94/05232 | 3/1994 |
| WO | WO 94/23327 | 10/1994 |
| WO | WO 95/02356 | 1/1995 |
| WO | WO 95/03747 | 2/1995 |
| WO | WO 95/08135 | 3/1995 |
| WO | WO 96/35397 | 11/1996 |
| WO | WO 97/28759 | 8/1997 |
| WO | WO 97/48004 | 12/1997 |
| WO | WO 97/48005 | 12/1997 |
| WO | WO 98/27896 | 7/1998 |
| WO | WO 98/48715 | 11/1998 |
| WO | WO 99/07309 | 2/1999 |
| WO | WO 00/25704 | 5/2000 |
| WO | WO 00/38594 | 7/2000 |
| WO | WO 00/51682 | 9/2000 |
| WO | WO 00/52516 A2 | 9/2000 |
| WO | WO 01/10641 A | 2/2001 |
| WO | WO 01/15779 | 3/2001 |
| WO | WO 01/17460 | 3/2001 |
| WO | WO 01/19364 | 3/2001 |
| WO | WO 01/82815 | 11/2001 |
| WO | WO 01/87189 | 11/2001 |
| WO | WO 02/13881 | 2/2002 |
| WO | WO 02/0027388 | 4/2002 |
| WO | WO 02/076320 | 10/2002 |
| WO | WO 02/102241 A2 | 12/2002 |
| WO | WO 03/001555 | 1/2003 |
| WO | WO 03/020177 | 3/2003 |
| WO | WO 03/022168 | 3/2003 |
| WO | WO 03/030763 A1 | 4/2003 |
| WO | WO 03/061518 A2 | 7/2003 |
| WO | WO 04/014969 | 2/2004 |
| WO | WO 04/034917 | 4/2004 |
| WO | WO 04/050132 | 6/2004 |
| WO | WO 04/105588 A2 | 12/2004 |
| WO | WO 2004/105588 | 12/2004 |
| WO | WO 2005/033263 | 4/2005 |
| WO | WO 2005/082265 | 9/2005 |
| WO | WO 2006/020638 | 2/2006 |
| WO | WO 06/047698 | 5/2006 |
| WO | WO 2006/047534 | 5/2006 |
| WO | WO 2006/060380 | 6/2006 |
| WO | WO 2006/113377 | 10/2006 |
| WO | WO 2006/113411 | 10/2006 |
| WO | WO 2006/113474 | 10/2006 |
| WO | WO 2006/113563 A1 | 10/2006 |
| WO | WO 2006/113564 A2 | 10/2006 |
| WO | WO 07/057734 | 5/2007 |
| WO | WO 2007/057734 | 10/2007 |
| WO | WO 2007/142981 | 12/2007 |
| WO | WO 2008/036671 | 3/2008 |
| WO | WO 2008/102096 | 8/2008 |
| WO | WO 2008/121649 | 10/2008 |
| WO | WO 2009/050511 | 4/2009 |

(56) References Cited

FOREIGN PATENT DOCUMENTS

| WO | WO 2009/122409 | 10/2009 |
|----|----------------|---------|
| WO | WO 2009/149060 | 12/2009 |
| WO | WO 2011/020074 | 2/2011 |
| WO | WO 2011/020078 | 2/2011 |
| WO | WO 2011/047076 | 4/2011 |
| WO | WO 2011/069059 | 6/2011 |
| WO | WO 2011/088107 | 7/2011 |
| WO | WO 2012/170066 | 12/2012 |
| WO | WO 2013/082545 | 6/2013 |
| WO | WO 2013/123265 | 8/2013 |
| WO | WO 2014/074610 | 5/2014 |
| WO | WO 2014/158653 | 10/2014 |

OTHER PUBLICATIONS

Accommodation and Presbyopia. Croft et al., International Opthalmology Clinics: Spring 2001, vol. 41, Issue 2, pp. 33-46.
Accomodation dynamics as a function of age. Heron et al. Ophthal. Physiol. Opt. 2002 22:389-396.
Accommodation Responses and Ageing. Heron et al. IOVS, Nov. 1999, vol. 40, No. 12, pp. 2872-2883.
Accommodative responses to anisoaccommodative targets. Koh et al. Ophthal. Physiol. Opt. vol. 18, No. 3, pp. 254-262, 1998.
Accommodation responses to flickering stimuli. Chauhan et al. Ophthal. Physiol. Opt. vol. 16. No. 5, pp. 391-408, 1996.
Accommodation to perceived depth in stereo tests. Koh et al. Ophthal. Physiol. Opt. vol. 18, No. 3, pp. 279-284, 1998.
Age Changes in the Interactions between the Accommodation and Vergence Systems. Heron et al. Optometry and Vision Science. vol. 78, No. 10, Oct. 2001.
Anterior Ciliary Sclerotomy for Treatment of Presbyopia: A Prospective Controlled Study. Hamilton et al. Ophthalmology, vol. 109, No. 11: Nov. 2002: pp. 1970-1977.
Barraquer, "Keratomileusis for Myopia and Aphakia", Ophthalmology, Rochester 88:701-708, 1981.
Binder et al., "Hydrogel keratophakia in non-human primates", Current Eye Research, vol. 1, No. 9, 1981/1982, pp. 535-542.
Brooks, J. et al., Identification of a vimentin-reactive Peptide associated with ocular lens membranes as cytokeratin, Ophthalmic Res., Jan.-Feb. 2003, pp. 8-11, vol. 35.
Cao et al., "Comparative study of the use of poly(glycolic acid), calcium alginate and pluronics in the engineering of autologous porcine cartilage", Polymers for Tissue Engineering, pp. 315-327, VSP 1998.
Can Accommodation be Surgically Restored in Human Presbyopia? Glasser, Adrian. Optometry and Vision Science, vol. 76, No. 9, Sep. 1999.
Changes in the static accommodation response with age. Kalsi et al. Ophthal. Physiol. Opt. vol. 21, No. 1, pp. 77-84, 2001.
Choice of Spatial Frequency for Contrast Sensitivity Evaluation After Corneal Refractive Surgery. Montes-Mico et al. Journal of Refractive Surgery, vol. 17: Nov./Dec. 2001: pp. 646-651.
Chow, C., et al., Broadband optical ultrasound sensor with a unique open-cavity structure, J. Biomed. Opt., Jan.-Feb. 2011, pp. 017001, vol. 16.
Choyce, P. "Implants with Coloured and Opaque Portions: Implants with Built-In Stenopeic Aperture," pp. 21-26 "Uniocular Aphakia Corrected by Anterior Chamber Implants with Built-In Stenopeic Aperture," pp. 132-136, 1964.
Clinical Characteristics of Lamellar Channel Deposits After Implementation of Intacs. Ruckhofer et al. J Cataract Refract Surg, vol. 26, Oct. 2000: pp. 1473-1479.
Contemporary Polymer Applications for Corneal Surgery. McCarey, Bernard E. pp. 504-505.
Cotliar et al., "Excimer Laser Radial Keratotomy", Ophthalmology, 1985.
Corneal Topography: The State of the Art, Alignment of Videokeratographs. Mandell et al. Chpt. 2, pp. 17-23, Jan. 1995.

"Corneal Surgery" by L. Girard, The C.V. Mosby Publishing Company, London 1981 pp. 107-141.
Dynamics of the accommodation response to abrupt changes in target vergence as a function of age. Heron et al. Vision Research 41 (2001) 507-519.
Dynamic retinoscopy and accomodation. Whitefoot et al. Ophthal. Physiol. Opt. vol. 12, Jan. 1992, pp. 8-17.
Eduard Jaeger's Test-Types (Schrift-Scalen) and Historical Development of Vision Tests. Runge, Paul E. Tr. Am. Ophth. Soc. vol. 98, 2000: 375.
Eight Years Experience with Permalens Intracorneal Lenses in Nonhuman Primates. Werblin et al. Refractive & Corneal Surgery, vol. 8, Jan./Feb. 1992, pp. 12-21.
"Epikeratophakia: Techniques, Compositions, and Clinical Results" by Werblin, Ophthalmology, 1983, pp. 45-58.
Errors in determining the direction of the visual axis in the presence of defocus. Atchison et al. Ophthal. Physiol. Opt., vol. 18, No. 5, pp. 463-467,1998.
Evaluate surgical routine to determine DLK cause, surgeon advises. Piechocki, Michael. Ocular Surgery News: Refractive Surgery, Jan. 1, 2003: p. 14.
Explanation for the observation of isogyres in crystalline lenses viewed between crossed polarizers. Ophthal. Physiol. Opt., vol. 13, Apr. 1993, pp. 209-211.
FDA Summary of Safety and Effectiveness Data for Tecnis Multifocal Posterior Chamber Intraocular Lens, Models ZM900 and ZMA00, 2009.
FDA Summary of Safety and Effectiveness Data for The Advanced Vision Science, Inc. XACT Foldable Hydrophopic Acrylic Ultraviolet Light-Absorbing Posterior Chamber Intraocular Lens (Model X-60 and Model X-70), 2009.
FDA Summary of Safety and Effectiveness Data for EC-3 IOL, (Models EC-3 IOL and EC-3 Precision Aspheric Lens), 2010.
FDA Summary of Safety and Effectiveness Data for Aaren Scientific's EC-3 IOL, 2010.
FDA Summary of Safety and Effectiveness Data for XACT Foldable Hydrophopic Acrylic UV Absorving Posterior Chamber Intraocular Lens discussing clinical investigation beginning on May 8, 2002.
Flap Measurements With the Hansatome Microkeratome. Spadea et al. Journal of Refractive Surgery, vol. 18, Mar./Apr. 2002: pp. 149-154.
Focused and divided attention in stereoscopic depth. Wickens et al. SPIE, vol. 1256 Stereoscopic Displays and Applications (1990); pp. 28-34.
Gamez, G., et al., Development of a pulsed radio frequency glow discharge for three-dimensional elemental surface imaging. 1. Application to biopolymer analysis, Anal. Chem., Feb. 2007, pp. 1317-1326, vol. 79.
Glasier, M., et al., A solid-phase assay for the quantitation of total protein eluted from balafilcon, lotrafilcon, and etafilcon contact lenses, Current Eye Research, 2008, pp. 631-640, vol. 33.
Griffith et al.; "Functional Human Corneal Equivalents Constructed from Cell Lines", SCIENCE, vol. 286, Dec. 10, 1999 pp. 2169-2172.
Groppi, J. J. "New Aspects in the Fitting of the Multi-Range Bifocal Contact Lens" Contacto, vol. 15:22-29 1971.
Guyton A.C., Textbook of Medical Physiology, $7^{th}$ Edition, W.B. Saunders Company, 1986: Chapter 58, pp. 700-710.
Hara, T., et al., Accommodative intraocular lens with spring action. Part 1. Design and placement in an excised animal eye, Ophthalmic Surg., Feb. 1990, vol. 21.
Hara, T., et al., Ten-year results of anterior chamber fixation of the posterior chamber intraocular lens, Arch. Ophthalmol., Aug. 2004, pp. 1112-1116.
Hayasaka, S., et al., Scanning electron microscopic study of polyvinylidene fluoride degradation by ocular tissue extracts, Jpn. J. Ophthalmol., 1984, pp. 131-135, vol. 28.
Hayashi, K., et al., Intraocular lens factors that may affect anterior capsule contraction, Ophthalmology, Feb. 2005, pp. 286-292, vol. 112.
Hayashi, K., et al., Comparison of decentration and tilt between one piece and three piece polymethyl methacrylate intraocular lenses, Br. J. Ophthalmol., Apr. 1998, pp. 419-422, vol. 82.

(56) References Cited

OTHER PUBLICATIONS

Hidaka, T. et al, Adaptive optics instrumentation in submillimeter/ terahertz spectroscopy with a flexible polyvinylidene fluoride cladding hollow waveguide, Rev. Sci. Instrum., 2007, pp. 25-26, vol. 78.
Hoffer et al., "UCLA Clinical Trial of Radial Keratotomy" Opthalmology, Aug. 1981; 88:729-736.
Holes in Clear Lenses Demonstrate a Pinhole Effect. Zacharia et al. Arch Ophthalmol, vol. 106, Apr. 1988, pp. 511-513.
Human Visual System—Image Formation, Encyclopedia of Imaging Science and Technology, Roorda, A., 2002, pp. 539-557.
Hybrid diffractive-refractive achromatic spectacle lenses. Charman, W. N. Ophthal. Physiol. Opt., vol. 14, Oct. 1994: pp. 389-392.
Iijima et al. "Formation of a spherical multicellular aggregate (spheroid) of animal cells in the pores of polyurethane foam as a cell culture substratum and its application to a hybrid artificial liver", Polymers for Tissue Engineering , pp. 273-286, VSP 1998.
Imaging in the 21st century. Charman, W. N. Ophthal. Physiol. Opt., vol. 18, No. 2, pp. 210-223, 1998.
International Preliminary Report on Patentability for PCT/US2014/020252 dated Sep. 15, 2015 in 10 pages.
International Search Report and Written Opinion for PCT/US2014/020252 dated Jul. 7, 2014 in 16 pages.
Intra-Ocular Lenses and Implants. Choyce, Peter. Chpts.4 & 17, 1964.
Intraocular pressure after excimer laser myopic refractive surgery. Montes-Mico et al. Ophthal. Physiol. Opt., vol. 21, No. 3, pp. 228-235, 2001.
Intrastromal Crystalline Deposits Following Hydrogel Keratophakia in Monkeys. Parks et al. Cornea, 12(1): 29-34, 1993.
Izak, A., et al., Loop memory of haptic materials in posterior chamber intraocular lenses, J. Cataract Refract. Surg., Jul. 2002, pp. 1129-1135, vol. 28.
"Katena Eye Instruments Catalog—Blaydes" dated Feb. 22, 2010, obtained from the Internet at: www.katena.com/html/product_detail.cfm in 1 page and printed on Feb. 22, 2010.
KENYON. "Recurrent Corneal Erosion: Pathogenesis and Therapy," 1978, pp. 169-195.
"Keratomileusis and Keratophakia in the Surgical Correction of Aphakia" by Barraquer, Cataract Surgery and Special Techniques, prior to 1996 pp. 270-289.
Khodadoust et al., "Adhesion of Regenerating Corneal Epithelium," Am. J. Of Opthalmology, Mar. 1968, pp. 339-348.
Kimura, W., et al., Comparison of shape recovery ratios in various IOL haptics, Nippon Ganka Gakkai Zasshi, Jun. 1991, pp. 548-555, vol. 95.
Kimura, W., et al., Comparison of shape recovery ratios in various intraocular lens haptics, J. Cataract. Refract. Surg., Nov. 1992, pp. 547-553, vol. 18.
Kimura, W., et al., Comparison of shape recovery ratios of single-piece poly(methyl methacrylate) intraocular lens haptics., J. Cataract. Refract. Surg., Sep. 1993, pp. 635-639, vol. 19.
Ko, A., et al. Seroreactivity against aqueous-soluble and detergent-soluble retinal proteins in posterior uveitis, Arch. Ophthalmol., Apr. 2011, pp. 415-420, vol. 129.
Kocak, N., et al., Intraocular lens haptic fracturing with the neodymium: YAG laser in vitro study, J. Cataract Refract. Surg., Apr. 2006, pp. 662-665, vol. 32.
Kruusing, A. Underwater and water-assisted laser processing: Part 2—Etching, cutting and rarely used methods. Optics and Lasers in Engineering, 2004: pp. 329-352.
"Lamellar Corneal Stromectomy for the Operative Treatment of Myopia" by Tadeusz Krwawicz, Notes, Cases, Instruments—1964, pp. 828-833.
Lipid Deposits Posterior to Impermeable Intracorneal Lenses in Rhesus Monkeys: Clinical, Histochemical, and Ultrastructural Studies. Rodrigues et al. Refractive & Corneal Surgery, vol. 6, Jan./Feb. 1990: DO. 32-37.
Lu Xuequan. Zhai Madlin, Li Jiuqiang, Ha Hongfei: "Radiation preparation and thermo-response swelling of interpenetrating polymer network hydrogel composed of PNIPAAm and PMMA" Radiation Physics and Chemistry, vol. 57, 2000, pp. 477-480, XP002473596.
Mastel Precision: Fiber Optic Ring Illuminator (Product Nos. 3776 & 4050) U.S. Pat. No. 5312393, User Manual. Rev: A02: Jan. 11, 1995, pp. 1-25.
Mastel Precision: The Ring Light. http://www.mastel.com/ring_light.html. Jul. 28, 2003.
Measurement of the wave-front aberration of the eye by a fast psychophysical procedure. He et al. J. Opt. Soc. Am. A, vol. 15, No. 9: Sep. 1998, pp. 2449-2455.
Microstructural Changes in Polyester Biotextiles During Implantation in Humans. King et al. NC State University: JTATM, vol. 1, Issue 3, Spring 2001, pp. 1-8.
Miller et al. "Quantification of the Pinhole effect" Perspectives in Refraction, vol. 21:347-350 1977.
Moran, C., et al. Polyvinylidene flouride polymer applied in an intraocular pressure sensor, Jpn. J. Appl. Phys., 2005, pp. L885-L887, vol. 44, Issue 27.
Near vision, lags of accommodation and myopia. Charman, W. N. Ophthal. Physiol. Opt., vol. 19, No. 2, pp. 126-133, 1999.
New Visual Acuity Charts for Clinical Research. Ferris et al. American Journal of Ophthalmology, 94: 91-96, 1982.
Night myopia and driving. Charman, W. N. Ophthal. Physiol. Opt., vol. 16, No. 6, p. 474-485, 1996.
Notch in contrast sensitivity function of optical origin: diffraction effects of acrylic filters. Irving et al., Ophthal. Physiol. Opt., vol. 13, Apr. 1993: pp. 179-182.
On modeling the causes of presbyopia. Glasser, A. Vision Research 41(2001) 3083-3087.
On the linearity of accommodation dynamics. Charman, W. N. Vision Research 40 (2000) 2057-2066.
Optical Aspects of Tolerances to Uncorrected Ocular Astigmatism. Charman et al. Optometry and Vision Science, vol. 70, No. 2: pp. 111-117, 1993.
Optical Modeling of Contact Lens Performance Final Report Covering Period Jul. 15, 1994-Mar. 31, 1995. Grivenkamp et al. for Pilkington Barnes Hind, Issued Apr. 5, 1995.
Optometric Clinical Practice Guideline Care of the Patient With Presbyopia: Reference Guide for Clinicians. Mancil et al. Mar. 20, 1998.
Ozanics et al., "Prenatal Development of the Eye and its Adnexa," Biomedical Foundation of Opthalmology, 1985, vol. 1, Chap 2, pp. 7-15.
Patel, C.K., et al. "Imaging the macula through a black occlusive intraocular lens". Arch. Ophthalmol. Oct. 2010; 128(10):1374-1376.
PermaVision intracorneal lens shows promise for hyperopia. Kronemyer, Bob. Ocular Surgery News: Jan. 1, 2003; p. 8.
Perspectives in Refraction: Quantification of the Pinhole Effect. Miller et al. Survey of Ophthalmology, vol. 21, No. 4, Jan./Feb. 1977, pp. 347-350.
Peyman et al., "Modification of Rabbit Corneal Curvature with use of Carbon Dioxide Laser Burns," Ophth, Surg., vol. 11, No. 5, 5/80, pp. 325-329.
Puliafito, C., et al., "Excimer Laser Ablator of the Cornea & Lens," Opthalmology, 6/85 vol. 92 No. 6, pp. 741-748.
Sally Pobojewski, "New U-developed laser performs high-precision corneal surgery", News and Information Services, The University Record, Jul. 16, 1997.
Poly(methyl methacrylate) model study of optical surface quality after excimer laser photo refractive keratectomy. Hauge et al. J Cataract Refract Surg., vol. 27, Dec. 2001, pp. 2026-2035.
Prince, S., et al., Sorption of alkylbenzyldimethylammonium chloride homologs to various filter media used in processing ophthalmics, APhA Annual Meeting, 1996, pp. 103, vol. 143.
Procyon: Marketing Information for Distributors: Pupil Measurement and Refractive Surgery (Samples from Academic Papers 1994 and 2002). pp. 1-17.
"Refractive Keratoplasty: Acute Morphologic Features," by Baumgarter et al, The CLAO Journal—Apr. 1985, vol. II, No. 2, pp. 163-169.
Refractive keratoplasty with intrastromal hydrogel lenticular implants. McCarey et al. Invest., Ophthalmol. Vis. ScL, Jul. 1981, pp. 107-115.

(56) References Cited

OTHER PUBLICATIONS

Retinal Image Quality in the Human Eye as a Function of the Accommodation. Lopex-Gil et al. Vision Research, vol. 38, No. 19, Jul. 3, 1998, pp. 1-11.
Rosenbloom "The Controlled-Pupil Contact Lens in Low Vision Problems" Journal of the American Optometric Association, pp. 836, 838, 840 1969.
Sato, "A New Surgical Approach to Myopia", Am. J. Ophthalmol. 36:823, 1953.
Shingleton, B., Reply: pupil stretch technique, J. Cataract Refract. Surg., 2007, pp. 362, vol. 33.
Simple parametric model of the human ocular modulation transfer function, A. Deeley et al. Ophthal. Physiol. Opt., vol. 11, Jan. 1991, pp. 91-93.
Karin R. Slettin, MD et al., "An In Vivo Model of Femtosecond Laser Intrastromal Refractive Surgery", Experimental Science, Ophthalmic Surgery and Lasers, Nov./Dec. 1999, vol. 30, No. 9, pp. 742-749.
Subjective Depth-of-Focus of the Eye. Atchison et al. Optometry and Vision Science, vol. 74, No. 7, Jul. 1997, pp. 511-520.
Subjective Sensitivity to Small Changes in the Contrast of a Suprathreshold Grating, The. Walsh et al. Vision Res., vol. 30, No. 1, pp. 163-193, 1990.
Surface Modification Properties of Parylene for Medical Applications, The. Wolgemuth, Lonny.Business Briefing: Medical Device Manfacturing & Technology 2002, pp. 1-4.
Surface tension control of collagen biomaterials by the selective hydrolysis of internal carboxyamides of the protein matrix. Revista Brasileira de Engenharia Biomedica, v. 15, n. 1-2, p. 55-61, jan/ago 1999.
Surgeon: Severe corneal lesions after LASIK are not stage 4 DLK. Piechocki, Michael. Ocular SurgeryNews; Jan. 1, 2003, pp. 16-17.
Subrayan, V., et al., Improving quality of vision with an anterior surface modified prolate intraocular lens: A prosepective clinical trial, Int. J. Ophthalmol., Aug. 2007, pp. 918-920, vol. 7, No. 4.
Swinger et al., "Keratophakia and Keratomileusis—Clinical Results", American Academy of Ophthalmology, Aug. 1981, vol. 88, No. 8, pp. 709-715.
Taboda, J. et al. "Response of the Corneal Epithelium to K.F. Excimer Laser Pulses," Health Physics, 1981, vol. 40, pp. 677-683.
Takahashi, E. "Use and Interpretation of the Pinhole Test" The Optometric Weekly, pp. 83-86 1965.
Tasaki, I., et al., Demonstration of heat production associated with spreading depression in the amphibian retina, Biochem. Biophys. Res. Commun., 1991, pp. 293-297, vol. 174.
Theoretical and practical performance of a concentric bifocal intraocular implant lens. Charman, W.N. Vision Research 38 (1998) 2841-2853.
Trokel, S., et al., "Excimer Laser Surgery of the Cornea," Am. J. Opthalmology, 1983 vol. 96, pp. 710-715.
Use of a digital infrared pupillometer to assess patient suitability for refractive surgery. Rosen et al. J Cataract Refract Surg., vol. 28: Aug. 2002. pp. 1433-1438.
Vision and driving—a literature review and commentary. Charman, W.N. Ophthal. Physiol. Opt., vol. 17, No. 5, pp. 371-391, 1997.
Wesley, N. K. "Research on the Multi-Range Lens," pp. 18-24, 1970.
Yamauchi et al., "Cultivation of fibroblast cells on keratin coated substrata", Polymers for Tissue Engineering, pp. 329-340, VS 1998.
Yusuf, et al., "Inability to perform posterior segment monitoring by scanning laser ophthalmoscopy or optical coherence tomography with some occlusive intraocular lenses in clinical use", J. Cataract Refract. Surg., Mar. 2012, 38: 513-513.
Yusuf, et al., "Occlusive IOLs for Intractable Diplopia Demonstrate a Novel Near-Infrared Window of Transmission for SLO/OCT Imaging and Clinical Assessment". Investigative Ophthalmology & Visual Science, May 2011, 52(6): 3737-3743.
Zavala et al., "Refractive Keratoplosty: Lathing and Cyropreservation," CLAO Journal, Apr. 1985, 11:155-162.

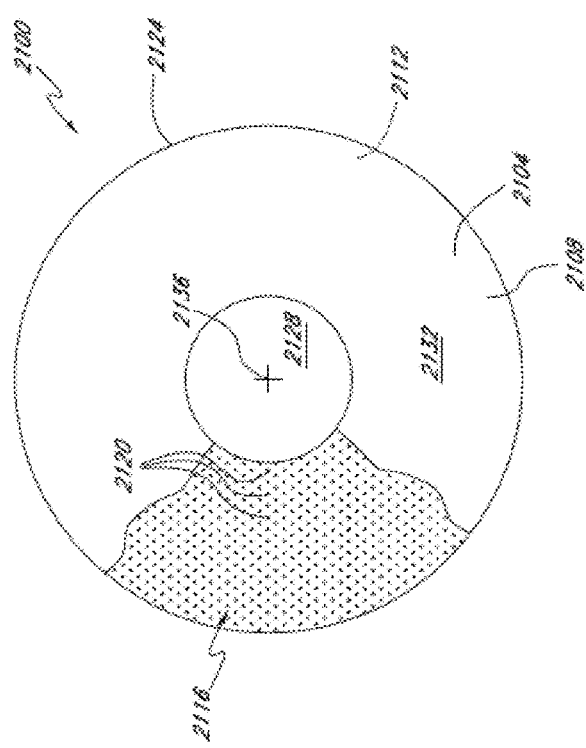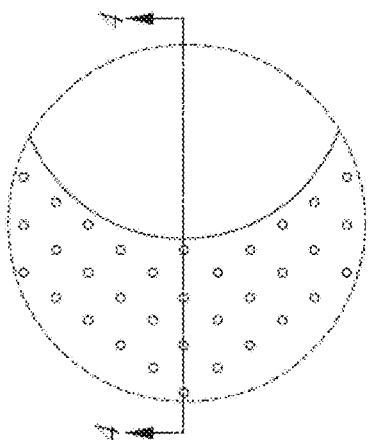

1

IN SITU ADJUSTABLE OPTICAL MASK

CROSS-REFERENCE TO RELATED APPLICATIONS

This application is a continuation of U.S. application Ser. No. 14/961,308, filed Dec. 7, 2015, which is a divisional of U.S. application Ser. No. 13/802,340, filed Mar. 13, 2013, now issued as U.S. Pat. No. 9,204,962. The entire contents of the aforementioned application and patent are hereby incorporated by reference.

BACKGROUND OF THE INVENTION

Field

This application relates generally to the field of ophthalmic devices. More particularly, this application is directed to corneal masks and intraocular implants, and methods of making the same.

Description of the Related Art

The human eye functions to provide vision by transmitting and focusing light through a clear outer portion called the cornea, and further refining the focus of the image onto a retina by way of a crystalline lens. The quality of the focused image depends on many factors including the size and shape of the eye, and the transparency of the cornea and the lens.

The optical power of the eye is determined by the optical power of the cornea and the crystalline lens. In a normal, healthy eye, sharp images of distant objects are formed on the retina (emmetropia). In many eyes, images of distant objects are either formed in front of the retina because the eye is abnormally long or the cornea is abnormally steep (myopia), or formed in back of the retina because the eye is abnormally short or the cornea is abnormally flat (hyperopia). The cornea also can be asymmetric or toric, resulting in an uncompensated cylindrical refractive error referred to as corneal astigmatism.

A normally functioning human eye is capable of selectively focusing on either near or far objects through a process known as accommodation. Accommodation is achieved by inducing deformation in a lens located inside the eye, which is referred to as the crystalline lens. Such deformation is induced by muscles called ciliary muscles. In most individuals, the ability to accommodate diminishes with age and these individuals cannot see up close without vision correction. If far vision also is deficient, such individuals are usually prescribed bifocal lenses.

SUMMARY OF THE INVENTION

For purposes of summarizing the disclosure, certain aspects, advantages and novel features of the invention have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

A first aspect of this application is directed toward an ophthalmic device comprising a mask configured to transmit substantially all visible light along an optical axis of the eye, the mask further comprising a transition portion configured to switch between at least a first degree of opacity and a second degree of opacity; and wherein the transition portion comprises a photochromic chromophore within a polymer matrix.

The mask may include an aperture configured to transmit substantially all visible light along the optical axis of the eye.

The mask may include a plurality of holes extending at least partially between an anterior surface of the mask and a posterior surface of the mask.

An intraocular lens may be coupled with the mask.

The first degree of opacity may allow transmission of substantially all visible light through the transition portion of the mask.

The second degree of opacity may prevent transmission of substantially all visible light through the transition portion of the mask.

The transition portion of the mask may comprise at least 50% of the total mask.

The transition portion may be configured to switch between a first degree of opacity and a second degree of opacity via application of both light and heat.

The polymer matrix may have a glass transition temperature of between 30-150° C.

The photochromic chromophore may comprise spiropyran.

Another aspect of this application is directed toward a method of switching the opacity of at least a portion of an ophthalmic device. The method includes providing a photochromic polymer mask with a controlled glass transition temperature, inserting the mask into an eye, and applying light and heat to the mask.

The heat may be applied via a laser, via ultrasonic energy or other energy modality for elevating the temperature of the mask.

A microscope can be used to monitor the photochromic polymer mask.

The glass transition temperature may be controlled by altering the chain length of the polymer.

The glass transition temperature may be controlled by altering the cross-link density of the polymer.

Another aspect of this application is directed toward a method of forming a mask portion. The mask includes a transition portion configured to switch between a first degree of opacity and a second degree of opacity and an aperture in the mask portion, the aperture configured to transmit substantially all visible light along an optical axis of an eye.

The method may include forming a plurality of holes in the mask portion, the plurality of holes extending at least partially between an anterior surface and a posterior surface of the mask.

The method may include coupling the mask portion with an intraocular lens.

The transition portion may include a photochromic chromophore contained within a polymer matrix.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIG. 3A depicts a top view of another embodiment of a mask configured to increase depth of focus.

FIG. 3B depicts an enlarged view of a portion of the view of 3B.

DETAILED DESCRIPTION

This application is directed to ocular devices and implants (e.g., masks) for improving the depth of focus of an eye of a patient and methods and apparatuses for making such ocular devices. The masks generally employ small-aperture vision correction methods to enhance depth of focus in a presbyopic eye thereby providing functional near vision. The masks can be applied to the eye in any manner and in any anterior-posterior location along the optical path, e.g., as an implant in the cornea (sometimes referred to as a "corneal inlay"). The masks can also be embodied in or combined with lenses and applied in other regions of the eye, e.g., as or in combination with contact lenses or intraocular lenses (IOL).

The ocular devices and masks described herein can be applied to masks and/or combined with features described in U.S. Patent Publication No. 2011/0040376, filed Aug. 13, 2010, entitled "MASKED INTRAOCULAR IMPLANTS AND LENSES," and International Patent Publication No. WO 2011/020074, filed Aug. 13, 2010, entitled "CORNEAL INLAY WITH NUTRIENT TRANSPORT STRUCTURES," hereby incorporated by reference in their entirety."

Figure 1B:
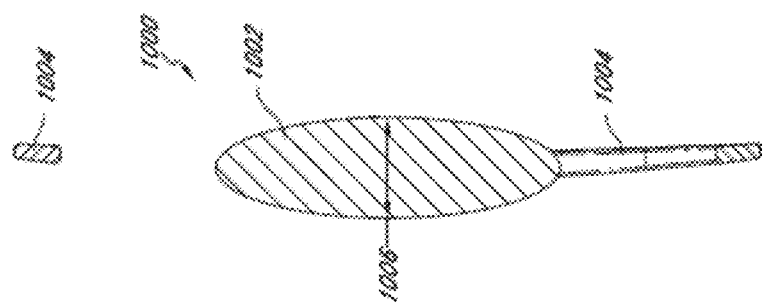
FIGS. 1A and 1B depict a conventional intraocular lens.
Figure 1A:
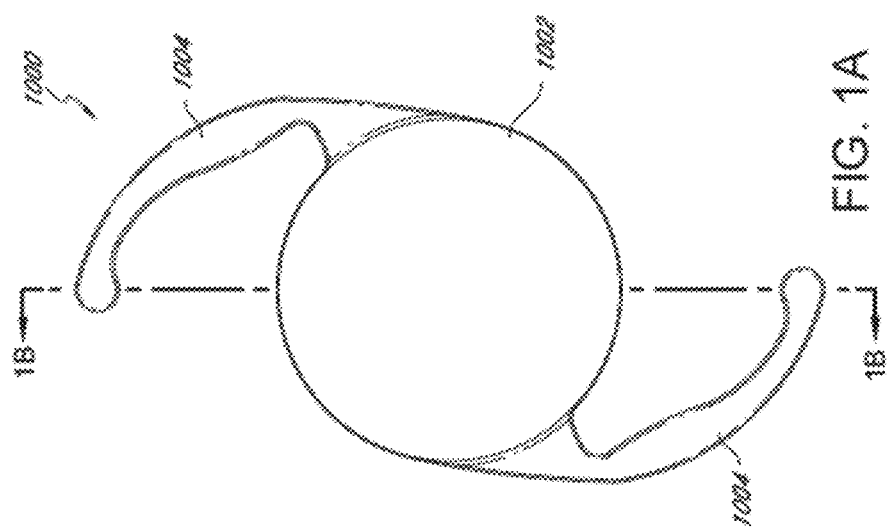

A conventional intraocular lens 1000 is illustrated in FIGS. 1A-B. The cross-sectional thickness of the lens body 1002 is generally dependent on the optical power of the intraocular lens 1000 and the material of the lens body 1002. In particular, the central region of the lens body 1002 is generally the thickest section of the intraocular lens 1000 with a central region cross-sectional thickness 1006. Methods for reducing the thickness of the intraocular lens are described in U.S. Pub. No. 2011/0040376, filed Aug. 13, 2010, hereby incorporated by reference in its entirety.

The intraocular lens and/or the lens body can be made from one or more materials. In certain embodiments, the intraocular lens and/or the lens body can comprise polymers (e.g. PMMA, PVDF, polypropylene, polycarbonate, PEEK, polyethylene, acrylic copolymers, polystyrene, PVC, polysulfone), hydrogels, and silicone).

Figure 2A:
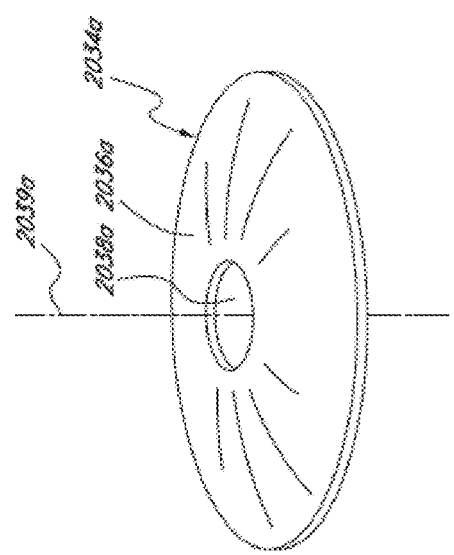
FIG. 2A is a perspective view of one embodiment of a mask.
Figure 2B:
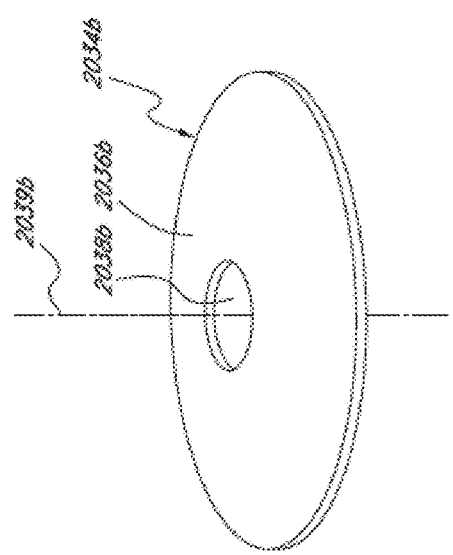
FIG. 2B is a perspective view of another embodiment of a mask.

A variety of variations of masks that can be used alone or positioned on or within the implant body are discussed herein, and also described in U.S. Pat. No. 7,628,810, U.S. Patent Publication No. 2006/0113054, and U.S. Patent Publication No. 2006/0265058, all of which are hereby incorporated by reference in their entirety. FIG. 2A illustrates one embodiment of a mask 2034a. The mask 2034a can include an annular region 2036a surrounding an aperture 2038a substantially centrally located on the mask 2034a. The aperture 2038a can be generally located around a central axis 2039a, referred to herein as the optical axis of the mask 2034a. The aperture 2038a can be in the shape of a circle. FIG. 2B illustrates another embodiment of a mask 2034b similar to the mask 2034a illustrated in FIG. 2A. The annular region 2036a of the mask 2034a of FIG. 2A has a curvature from the outer periphery to the inner periphery of the annular region 2036a, such that the annular region 2036a substantially conforms to the surface of a geometry of rotation, such as a sphere. The annular region 2036b of the mask 2034b of FIG. 2B is substantially flat.

The mask can have a constant thickness. However, in some embodiments, the thickness of the mask can vary between the inner periphery (near the aperture 2038a,b) and the outer periphery.

The mask can have dimensions configured to improve a patient's vision. For example, if the mask is embedded within the implant body, the thickness of the mask can vary depending on the location of the mask relative to the implant body. For example, the mask can have a thickness greater than zero and less than the thickness of the implant body. Alternatively, if the mask is coupled to a surface of the implant body, the mask can preferably have a thickness no greater than necessary to have desired opacity so that the mask does not add additional thickness to the intraocular lens. In certain embodiments, the mask has a thickness of greater than zero and less than about 0.5 mm. In some embodiments, the mask has a thickness of at least about 0.25 mm and/or less than or equal to about 0.3 mm. In some embodiments, the mask has a thickness of at least 0.005 mm and/or less than or equal to about 0.015 mm. In one embodiment, the mask has a thickness of about 0.25 mm. If the mask is on or near the surface of a transition zone, as described in U.S. Pub. No. 2011/0040376, filed Aug. 13, 2010 and hereby incorporated by reference in its entirety, the mask can have a shape similar or the same as the transition zone.

The annular region 2036a,b can be at least partially opaque or can be completely opaque to visible light. The degree of opacity of the annular region 2036a,b prevents at least some or substantially all light from being transmitted through the mask 2034a,b. Generally, transmission of light through the annular region will be no more than about 5%, often no more than about 3% and in some applications, no more than about 1%. Opacity of the annular region 2036a,b can be achieved in any of several different ways.

For example, in one embodiment, the material used to make mask 2034a,b can be naturally opaque. Alternatively, the material used to make the mask 2034a,b can be substantially clear, but treated with a dye or other pigmentation agent to render region 2036 substantially or completely opaque. In still another example, the surface of the mask 2034 can be treated physically or chemically (such as by etching) to alter the refractive and transmissive properties of the mask 2034a,b and make it less transmissive to light.

The material of the mask 2034a,b can be, for example, any of a variety of polymeric materials. Where the mask 2034a,b is applied to or fixed within the intraocular implant, the material of the mask 2034 should be biocompatible. Examples of suitable materials for the mask 2034a,b include the preferred PVDF, other suitable polymers or co-polymers, such as hydrogels, or fibrous materials, such as a Dacron mesh.

In additional embodiments, a photochromic material can be used as the mask or as a variable transmission zone in addition to a non-photochromic or non-variable transmission zone of the mask. Under bright light conditions, the photochromic material can darken thereby creating a mask (having a transmission aperture) and enhancing near vision. Under dim light conditions, the photochromic material lightens, which allows more light to pass through to the retina. In certain embodiments, under dim light conditions, the photochromic material lightens to expose an optic of the intraocular implant. Further photochromic material details are disclosed in U.S. patent application Ser. No. 13/691,625, filed Nov. 30, 2012, which is hereby incorporated by reference in its entirety.

The mask can have different degrees of opacity. For example, the mask can block substantially all of visible light or can block a portion of visible light. The opacity of the mask can also vary in different regions of the mask. In certain embodiments, the opacity of the outer edge and/or the inner edge of the mask is less than the central region of the mask. The opacity in different regions can transition abruptly or have a gradient transition. Additional examples of opacity transitions can be found in U.S. Pat. Nos. 5,662,706, 5,905,561 and 5,965,330, all of which are hereby incorporated by reference in their entirety.

Further mask details are disclosed in U.S. Pat. No. 4,976,732, issued Dec. 11, 1990, U.S. Pat. No. 7,628,810, issued Dec. 8, 2009, and in U.S. patent application Ser. No. 10/854,032, filed May 26, 2004, all of which are hereby incorporated by reference in their entirety.

An advantage to embodiments that include a mask with an aperture (e.g., pin-hole aperture) described herein over multifocal IOLs, contact lenses, or refractive treatments of the cornea is that all of these latter approaches divide the available light coming through the aperture into two or more foci while a mask approach has a single focus (monofocal). This limitation forces designers of multifocal optics to choose how much of the light is directed to each focal point, and to deal with the effects of the unfocused light that is always present in any image. In order to maximize acuity at the important distances of infinity (>6M) and 40 cm (normal reading distance), it is typical to provide little or no light focused at an intermediate distance, and as a result, visual acuity at these distances is poor. With a mask that includes an aperture to increase depth-of-focus, however, the intermediate vision of presbyopic patients is improved significantly. Indeed, the defocus blur with the aperture is less at intermediate distances than at near.

Figure 4:
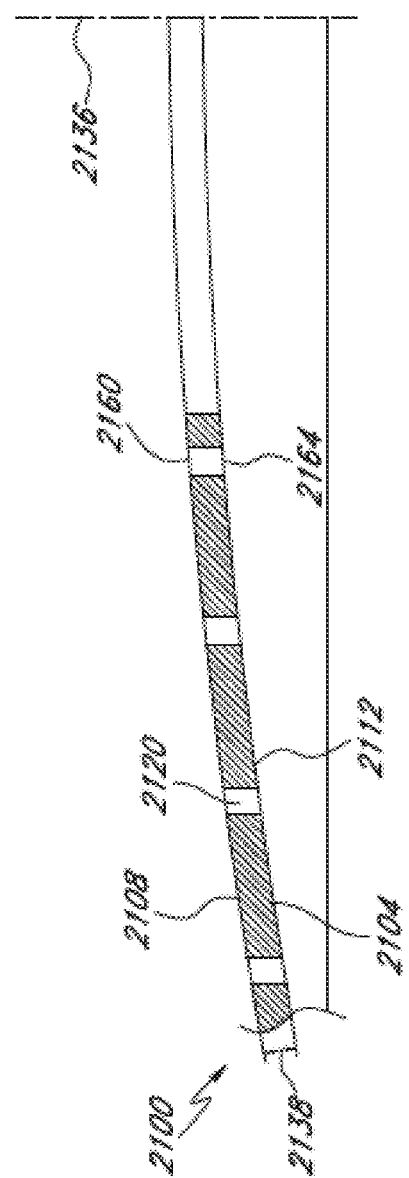
FIG. 4 is a cross-sectional view of the mask of FIG. 3B taken along the section plane 4-4.

FIGS. 3-4 show another embodiment of a mask 2100 configured to increase depth of focus of an eye of a patient with presbyopia. The mask 2100 is similar to the masks hereinbefore described, except as described differently below. The mask 2100 can be made of the materials discussed herein, including those discussed above. In addition, the mask 2100 can be formed by any suitable process. The mask 2100 is configured to be applied to an IOL.

In one embodiment, the mask 2100 includes a body 2104 that has an anterior surface 2108 and a posterior surface 2112. The body 2104 can be formed of any suitable material, including at least one of an open cell foam material, an expanded solid material, and a substantially opaque material. In one embodiment, the material used to form the body 2104 has relatively high water content. In other embodiments, the materials that can be used to form the body 2104 include polymers (e.g. PMMA, PVDF, polypropylene, polycarbonate, PEEK, polyethylene, acrylic copolymers (e.g., hydrophobic or hydrophilic), polystyrene, PVC, polysulfone), hydrogels, silicone, metals, metal alloys, or carbon (e.g., graphene, pure carbon).

In one embodiment, the mask 2100 includes a hole arrangement 2116. The hole arrangement 2116 can comprise a plurality of holes 2120. The holes 2120 are shown on only a portion of the mask 2100, but the holes 2120 preferably are located throughout the body 2104 in one embodiment. The mask 2100 has an outer periphery 2124 that defines an outer edge of the body 2104. In some embodiments, the mask 2100 includes an aperture 2128 at least partially surrounded by the outer periphery 2124 and a non-transmissive or reduced transmissive portion 2132 located between the outer periphery 2124 and the aperture 2128.

Preferably the mask 2100 is symmetrical, e.g., rotationally symmetrical about a mask axis 2136. In one embodiment, the outer periphery 2124 of the mask 2100 is circular. The mask in general has an outer diameter of at least about 3 mm and/or less than about 6 mm. In some embodiments, the mask is circular and has a diameter of at least about 3 mm and/or less than or equal to about 4 mm. In some embodiments, the mask 2100 is circular and has a diameter of about 3.2 mm. In some embodiments, masks that are asymmetrical or that are not symmetrical about a mask axis provide benefits, such as enabling a mask to be located or maintained in a selected position with respect to the anatomy of the eye.

The body 2104 of the mask 2100 can be configured to be coupled with a particular intraocular lens design, either of reduced thickness design or of conventional design. For example, where the mask 2100 is to be coupled with a particular IOL that has curvature, the body 2104 can be provided with a corresponding amount of curvature along the mask axis 2136 that corresponds to the curvature. Likewise, the body 2104 can be provided with corresponding shape to accommodate IOL transition zones. Further details about the reduced thickness design are described in U.S. Pub. No. 2011/0040376, filed Aug. 13, 2010 and hereby incorporated by reference in its entirety.

In one embodiment, one of the anterior surface 2108 and the posterior surface 2112 of the body 2104 is substantially planar. In one planar embodiment, very little or no uniform curvature can be measured across the planar surface. In another embodiment, both of the anterior and posterior surfaces 2108, 2112 are substantially planar. In general, the thickness of the body 2104 of the mask 2100 can be within the range of from greater than zero to about 0.5 mm, about 1 micron to about 40 microns, and often in the range of from about 5 microns to about 20 microns. In some embodiments, the body 2104 of the mask 2100 has a thickness 2138 of at least about 5 microns and/or less than or equal to about 20 microns. In some embodiments, the body 2104 of the mask has a thickness 2138 of at least about 10 microns and/or less than or equal to about 15 microns. In certain embodiments, the thickness 2138 is about 15 microns. In certain embodiments, the thickness 2138 is about 10 microns. In certain embodiments, the thickness 2138 of the mask 2100 is about 5 microns. In another embodiment, the thickness 2138 of the mask 2100 is about 8 microns. In another embodiment, the thickness 2138 of the mask 2100 is about 10 microns.

A substantially planar mask has several advantages over a non-planar mask. For example, a substantially planar mask can be fabricated more easily than one that has to be formed to a particular curvature. In particular, the process steps involved in inducing curvature in the mask 2100 can be eliminated.

The aperture 2128 is configured to transmit substantially all incident light along the mask axis 2136. The non-transmissive portion 2132 surrounds at least a portion of the aperture 2128 and substantially prevents transmission of incident light thereon. As discussed in connection with the above masks, the aperture 2128 can be a through-hole in the body 2104 or a substantially light transmissive (e.g., transparent) portion thereof. The aperture 2128 of the mask 2100 generally is defined within the outer periphery 2124 of the mask 2100. The aperture 2128 can take any of suitable configurations, such as those described above.

In one embodiment, the aperture 2128 is substantially circular and is substantially centered in the mask 2100. The size of the aperture 2128 can be any size that is effective to increase the depth of focus of an eye of a patient with presbyopia. In particular, the size of the aperture 2128 is dependent on the location of the mask within the eye (e.g., distance from the retina). In some embodiments, the aperture 2128 can have a diameter of at least about 0.85 mm and/or less than or equal to about 2.2 mm. In certain embodiments, the diameter of the aperture 2128 is less than about 2 mm. In some embodiments, the diameter of the aperture is at least about 1.1 mm and/or less than or equal to about 1.6 mm. In a further embodiment, the diameter of the aperture is at least about 1.3 mm and/or less than or equal to about 1.4 mm.

In certain embodiments, the aperture 2128 includes an optical power and/or refractive properties. For example, the aperture 2128 can include an optic and can have an optical power (e.g. positive or negative optical power). In certain embodiments, the aperture 2128 can add to the active correction of the intraocular lens.

The non-transmissive portion 2132 is configured to prevent transmission of visible light through the mask 2100. For example, in one embodiment, the non-transmissive portion 2132 prevents transmission of substantially all of at least a portion of the spectrum of the incident visible light. In one embodiment, the non-transmissive portion 2132 is configured to prevent transmission of substantially all visible light, e.g., radiant energy in the electromagnetic spectrum that is visible to the human eye. The non-transmissive portion 2132 can substantially prevent transmission of radiant energy outside the range visible to humans in some embodiments.

As discussed above, preventing transmission of light through the non-transmissive portion 2132 decreases the amount of light that reaches the retina and the fovea that would not converge at the retina and fovea to form a sharp image. As discussed above, the size of the aperture 2128 is such that the light transmitted therethrough generally converges at the retina or fovea. Accordingly, a much sharper image is presented to the retina than would otherwise be the case without the mask 2100.

In one embodiment, the non-transmissive portion 2132 prevents transmission of at least about 90 percent of incident light. In another embodiment, the non-transmissive portion 2132 prevents transmission of at least about 95 percent of all incident light. The non-transmissive portion 2132 of the mask 2100 can be configured to be substantially opaque to prevent the transmission of light.

In some embodiments, the non-transmissive portion 2132 can transmit no more than about 5% of incident visible light. In some embodiments, the non-transmissive portion 2132 can transmit no more than about 3% of incident visible light. In some embodiments, the non-transmissive portion 2132 can transmit no more than about 2% of incident visible light.

In one embodiment, at least a portion of the body 2104 is configured to be opaque to more than 99 percent of the light incident thereon.

As discussed above, the non-transmissive portion 2132 can be configured to prevent transmission of light without absorbing the incident light. For example, the mask 2100 could be made reflective or could be made to interact with the light in a more complex manner, as discussed in U.S. Pat. No. 6,554,424, issued Apr. 29, 2003, which is hereby incorporated by reference in its entirety.

As discussed above, the mask 2100 can include a plurality of holes 2120. The lens body can extend at least partially through the holes, thereby creating a bond (e.g. material "bridge") between the lens body on either side of the mask.

The holes 2120 of the mask 2100 shown in FIG. 3A can be located anywhere on the mask 2100. In some embodiments, substantially all of the holes are in one or more regions of a mask. The holes 2120 of FIG. 3A extend at least partially between the anterior surface 2108 and the posterior surface 2112 of the mask 2100. In one embodiment, each of the holes 2120 includes a hole entrance 2160 and a hole exit 2164. The hole entrance 2160 is located adjacent to the anterior surface 2108 of the mask 2100. The hole exit 2164 is located adjacent to the posterior surface 2112 of the mask 2100. In one embodiment, each of the holes 2120 extends the entire distance between the anterior surface 2108 and the posterior surface 2112 of the mask 2100. Further details about possible hole patterns are described in WO 2011/020074, filed Aug. 13, 2010, incorporated by reference above.

In some embodiments, the mask 2100 can include an annular region near the outer periphery 2124 of the mask having no holes. In certain embodiments, there are no holes within 0.1 mm of the outer periphery 2124 of the mask 2100.

In some embodiments, the mask can include an annular region around the inner periphery of the mask having no holes. In certain embodiments, there are no holes within 0.1 mm of the aperture 2128.

Figure 5:
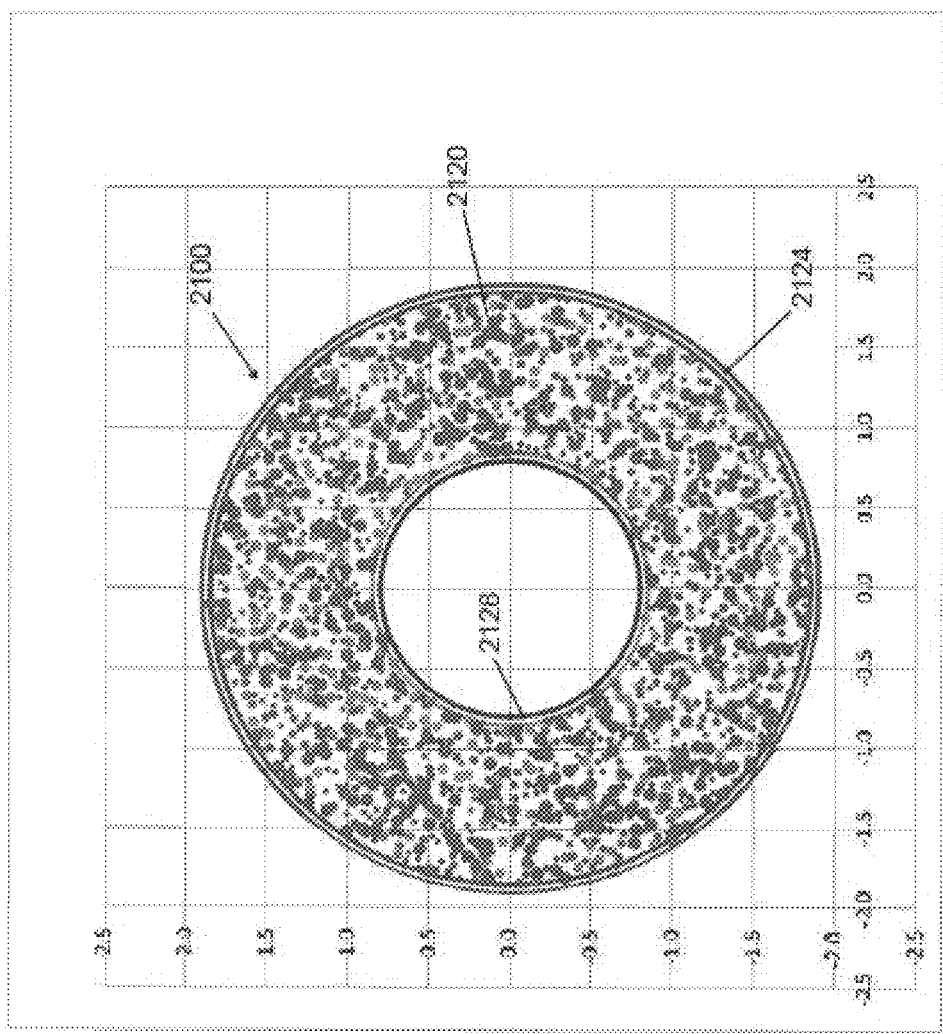
FIG. 5 is a graphical representation of one arrangement of holes of a plurality of holes that can be formed in an ophthalmic device.

As shown in FIG. 5, the mask 2100 can include a plurality of holes 2120. In some embodiments, the holes 2120 each have a same diameter. In certain embodiments, the holes 2120 can include one or more different diameters. In some embodiments, the diameter of any single hole 2120 is at least about 0.01 mm and/or less than or equal to about 0.02 mm. In some embodiments, the diameter of the holes 2120 can include one or more of the following hole diameters: 0.010 mm, 0.013 mm, 0.016 mm, and/or 0.019 mm.

In some embodiments, the holes are interspersed at irregular locations throughout at least a portion of the mask 2100. In some embodiments, holes of different diameters are evenly interspersed throughout at least a portion of the mask 2100. For example, the mask 2100 can include a plurality of non-overlapping hole regions. The sum of the surface area of the plurality of non-overlapping hole regions can equal to total surface area of the entire hole region of the mask. Each region of the plurality of regions can include a number of holes, each of the holes having a different diameter. The number of holes in each region can equal the number of different hole sizes in the entire hole region.

In some embodiments, there are at least about 1000 holes and/or less than or equal to about 2000 holes. In some embodiments, there are at least about 1000 holes and/or less than or equal to about 1100 holes. In some embodiments, there are about 1040 holes. In some embodiments, there are an equal number of holes of each diameter. In some embodiments, the number of holes having each diameter is different.

Figure 6B:
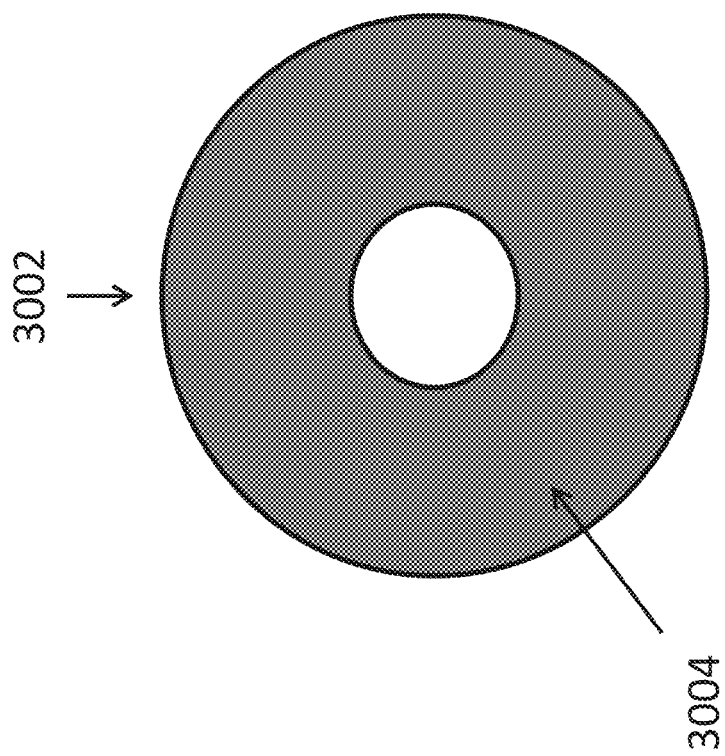
FIGS. 6A and 6B depict an embodiment of a mask that switches between one level of opacity and another level of opacity.
Figure 6A:
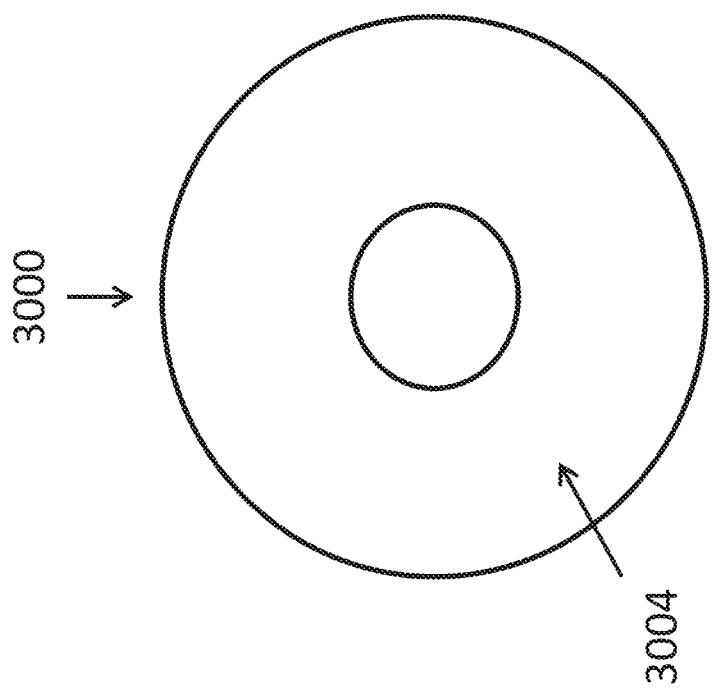

FIG. 6A-6B depicts one embodiment of a switchable mask where at least a portion of the mask, hereby referred to as the transition portion, is configured to switch between different levels of opacity to allow different amounts of light to pass through the mask. For example, the transition portion can switch between lower degrees of opacity 3000 to higher degrees of opacity 3002. In this illustrative embodiment, the mask contains photochromic chromophores within a polymer matrix 3004. Although initially substantially colorless, when the photochromic chromophores are allowed to freely rotate and are further exposed to certain activating wavelengths of light, the molecules will rotate into a conformation that absorbs some amount of visible light. However, when the activating light source is removed, the molecules will relax and return to a substantially colorless state. It is particularly advantageous to lock these molecules into one state or another, to prolong the visible light blocking aspect of the molecules. Further, it is advantageous to be able to controllably switch the chromophores between a locked colorless state, wherein visible light can be freely transmitted, to a locked state that absorbs visible light and back again.

In certain embodiments, the free rotation of the photochromic chromophores can be prevented by using particular mask materials such as a photochromic polymer, wherein photochromic chromophores are contained within a polymer matrix. To further control the rotation of the photochromic chromophores, such a polymer matrix can have a controlled glass transition temperature (Tg), such that when heat is applied to the polymer matrix, the matrix undergoes a glass transition from a brittle to a more molten or rubber-like state. While in the more brittle state, the polymer matrix prevents free rotation of the photochromic chromophore, locking the photochromic chromophore into a colorless or a light-absorbing state. However, when in the less brittle, more molten state, the polymer matrix allows free rotation of the photochromic chromophore between colorless or light-absorbing states. Consequently, in this embodiment, a mask can be configured to switch between a state with one degree of opacity to a state with another degree of opacity, through the simple application of heat and activating light.

Figure 7:
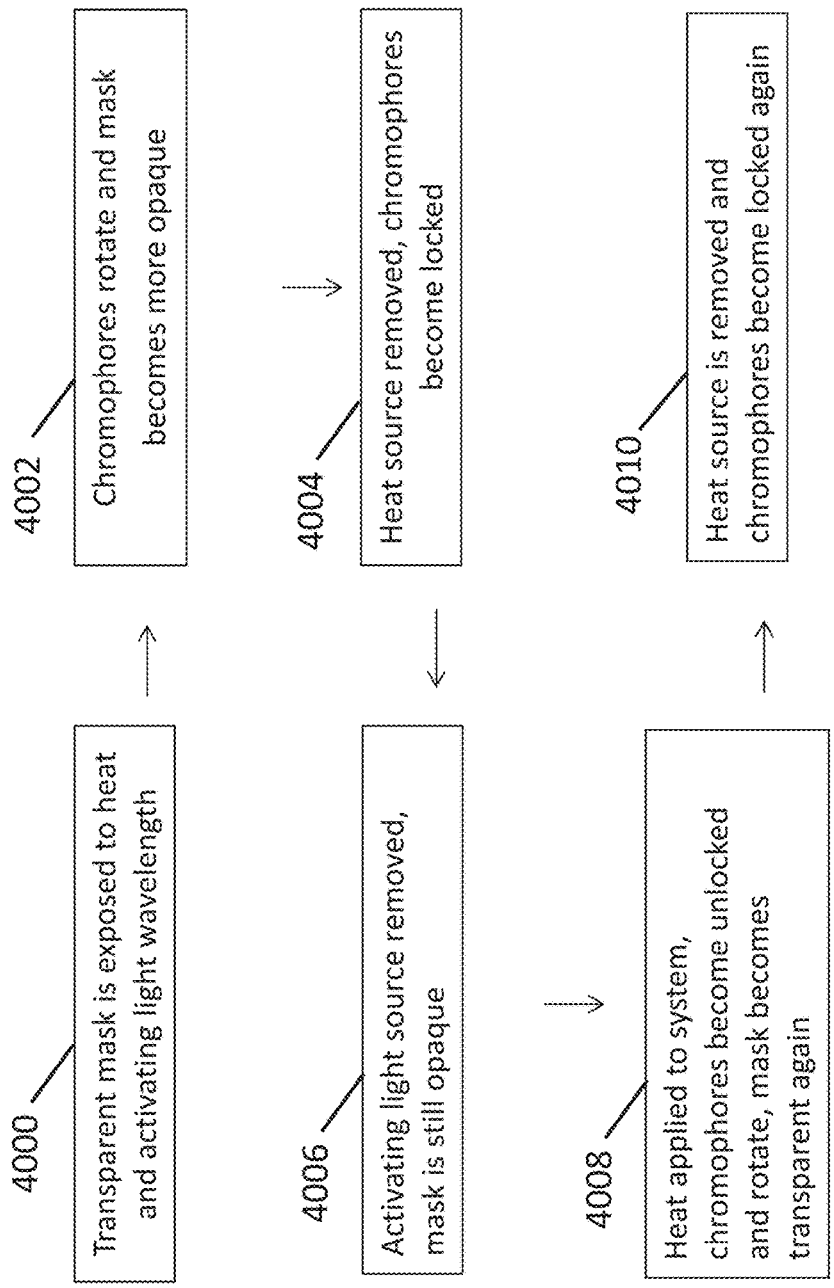
FIG. 7 is a flowchart that depicts one embodiment of a method for switching the opacity of a transition portion of a mask.

FIG. 7 is a flowchart illustrating an embodiment of a method for controlling the opacity of a photochromic polymer mask configured to switch between different levels of opacity. At step 4000, a switchable mask implanted in the eye is exposed to both heat and an activating light source. The exposure to heat causes the polymer matrix to undergo a glass transition while the light activation of the photochromic chromophores causes the molecules to rotate and absorb visible light, causing the transition portion on the mask to become more opaque 4002. In step 4004, the heat source is removed and the polymer matrix undergoes a glass transition back to a more brittle form, thus locking in the light-absorbing photochromic chromophores so that they can no longer rotate, resulting in retention of the enhanced opacity of the transition portion. In step 4006, the activating light source is removed; however the mask remains opaque because the energy-activated photochromic chromophores are not able to freely rotate back into a relaxed colorless state. In optional step 4008, heat is again applied to the mask, causing the polymer matrix to again undergo a glass transition. This glass transition allows the photochromic chromophores to freely rotate back into their relaxed, colorless state, causing the mask to become less opaque. In optional step 4010, the heat source is removed from the mask and the polymer matrix undergoes a glass transition back to a more brittle state, locking the photochromic chromophores into a non-rotatable state. Thus, in this example, the mask has been switched from a state with one degree of opacity to a state with another degree of opacity and back again, by the application of heat and activating light.

In some embodiments, a mask configured to controllably switch between different levels of opacity is advantageous because it can allow treatment providers to inspect the back of the eye without requiring the removal of the mask. Further, in certain embodiments, such a feature can allow for switchable changes in mask geometry from outside the eye, potentially allowing for the adjustment of the masks from a first opacity to a second different opacity for various treatments or performance objectives.

In some embodiments, the transition portion of the mask can comprise any proportion of the total mask, ranging from above 0% to 100% of the mask. For example, the transition portion can be at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, or about 100% of the total area of the opaque portion of the mask.

In certain embodiments, the transition portion can switch between a first level of opacity that blocks the transmittance of substantially all light and a second level of opacity where substantially all light can pass through the mask. In some embodiments, the mask can be configured to switch between any level of opacity ranging from above 0 to 100%, corresponding to blocking between 0% to 100% of visible light, respectively. For example, the change in the level of opacity between the first level and the second level can be at least about 5%, at least about 10%, at least about 15%, at least about 20%, at least about 30%, at least about 40%, at least about 50%, at least about 60%, at least about 70%, at least about 80%, or more.

Figures 8A, 8B, 8C, 8D, 8E, 8F:
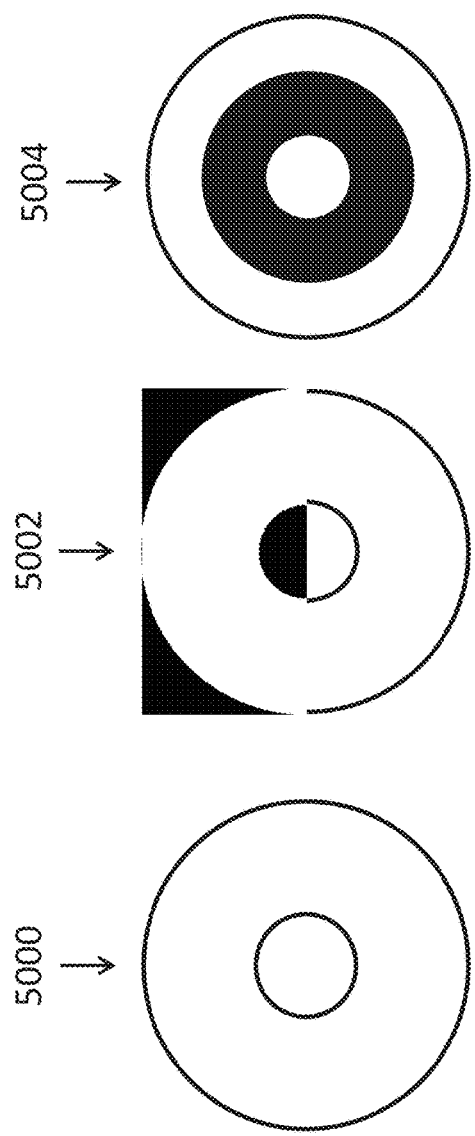
FIGS. 8A-8F depict multiple embodiments of various geometries of the transition portions of a mask.

FIGS. 8A-8F depict embodiments of various geometric configurations for the transition portion of the mask. For example, the switchable portion of the mask can switch between a uniform high transmission 5000 (FIG. 8A) and another degree of opacity via switching of a portion of the mask such as in the top half 5002 (FIG. 8B) or an inner annulus 5004 (FIG. 8C), or the entire mask such as in 5006 (FIG. 8D) and 5008 (FIG. 8E). In further embodiments, multiple transition portions are configured to switch between various levels of opacity 5010 (FIG. 8F).

For example, referring to FIG. 8F, a mask 5010 having a central aperture 5012 is illustrated. A first annular zone 5014 surrounds the aperture 5012. A second annular zone 5016 surrounds the first annular zone 5014. A third annular zone (not illustrated) may surround the second annular zone 5016. Each of the annular zones may comprise a homogeneous optical transmission characteristic, or may comprise an annular ring of two or more alternating or intermittent sections having distinct absorption characteristics.

In one implementation of the invention, the outer annular ring 5016 comprises a fixed opacity. The inner ring 5014 comprises a transition portion as described elsewhere herein. The opacity of the transition portion may be adjusted between a first opacity that is relatively high, such as substantially equivalent to the opacity of the outer zone 5016, and a reduced opacity as described elsewhere herein. In effect, the invention enables the provision of a mask 5010 having an aperture 5012 of a first diameter. Adjustment of the opacity of the inner ring 5014 from a relatively high opacity to a relatively low opacity has the effect of increasing the diameter of the central aperture 5012. This may be desirable for altering the optical characteristics of the mask, or for increasing the visual access to the interior of the eye for diagnostic or therapeutic purposes.

Alternatively, the relationship between the fixed ring and the variable ring may be reversed. Thus, the inner ring 5014 may be provided with a permanent opacity. The outer ring 5016 may be provided with a variable characteristic such that the opacity may be changed between a relatively low level and a relatively high level.

In general, the mask of the present invention may be provided on an intraocular lens, a corneal inlay, or elsewhere along the optical path. It may be provided with at least a first region having a predetermined transmission characteristic, and at least a second region having a controllable variable transmission characteristic.

The variable opacity characteristic can be accomplished by any of a variety of systems in which a change in opacity may be accomplished in response to exposure to an external stimulus. The external stimulus can be ultraviolet, visible or infrared light, heat, a radiofrequency or magnetic field, electrical current, mechanical vibration (e.g. ultrasound) or other triggering signal that can be applied to the eye. Certain chemical systems which respond to an exposure to light will be described further herein.

As described above, in some embodiments, the mask contains at least one transition portion with photochromic chromophores contained within a polymer matrix. In a preferred embodiment, the photochromic chromophore is spiropyran, although other photochromic chromophores can be used. For example, any photochromic chromophore that undergoes a stereochemical conformational change that can be locked within a polymer matrix can be used. In certain embodiments, the photochromic chromophore or other compound can be any suitable molecule or compound that can be bound into a polymer chain. Further suitable chromophores include, but are not limited to: naphthopyrans, chromenes, fulgides, similar molecules, and mixtures thereof. In other embodiments, dimers of the photochromic chromophore can be used such as, for example, a spiropyran dimer. Desirably, in embodiments, the photochromic chromophore or compound is one that can easily rearrange in the photochromic polymer to alter the transmission state when exposed to suitable irradiation and heat, but which is more difficult to rearrange in the photochromic polymer to alter the transmission state when heat is removed. For example, further details concerning the use of photochromic chromophores within a polymer matrix can be found in U.S. Pat. No. 8,216,765, entitled "REIMAGEABLE AND REUSABLE MEDIUM AND METHOD OF PRODUCING AND USING THE REIMAGEABLE AND REUSABLE MEDIUM," filed Mar. 9, 2009, and which is hereby incorporated by reference in its entirety.

In certain embodiments, the photochromic chromophore concentration within the polymer matrix of the transition portion can be varied to result in a range of switchable opacities. For example, the concentration of photochromic chromophore can be varied to produce a switchable level of opacity within the transition portion having a change in transmission of at least about 5%, at least about 10%, at least about 20%, at least about 30%, at least about 40%, at least 50%, at least about 60%, at least about 70%, or more between the high transmission and low transmission states.

In some embodiments, the photochromic chromophore can be distributed homogenously throughout the transition portions of the mask, resulting in a constant level of opacity across the transition portions of the mask. In certain embodiments, the photochromic chromophore can be distributed heterogeneously throughout the transition portions of the mask, resulting in a non-constant level of opacity across the transition portions of the mask.

In some embodiments, the wavelength of light used to activate the photochromic chromophore to switch from a colorless or high transmission state to an opaque or relatively lower transmission state can be any wavelength of light capable of triggering an absorption transition. In certain embodiments, the wavelength of light used to activate the photochromic chromophore to switch from a colorless state to an opaque state is in the ultraviolet range. In further embodiments, the wavelength of light used to activate the photochromic chromophore is in the infrared range. In additional embodiments, the wavelength of light used to activate the photochromic chromophores is in the visible light range.

In certain embodiments, the photochromic chromophore contained within the transition portion of the mask can be selected so as to allow for exposure to selected events such as illumination and imaging via a camera without activating the photochromic chromophore. For example, the wavelength of light used by the camera to illuminate and image the mask can be of such a different wavelength of light from the activating wavelength of the photochromic chromophore that the light from the camera will not activate the photochromic chromophore. In some embodiments, near infrared light could be used by the camera, while ultraviolet light is used for the photochromic chromophore.

In certain embodiments, the wavelength of energy used by the illuminating and imaging camera is the same as the wavelength of energy used to heat the system. In some embodiments, the wavelength of energy used by the camera is different from the wavelength of energy used to heat the system.

Figure 9:
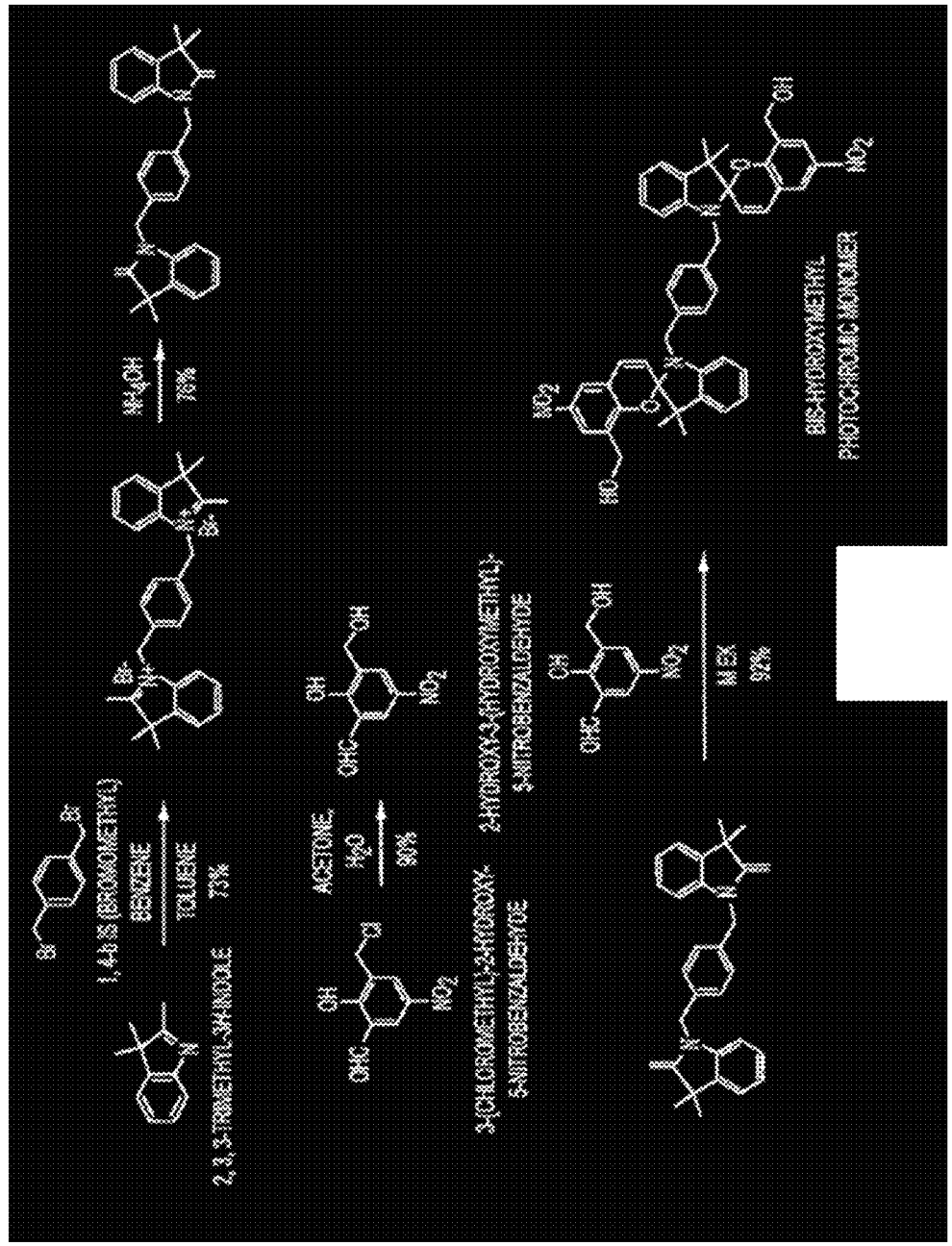
FIG. 9 depicts one embodiment of the synthesis of a photochromic monomer.
Figure 10:
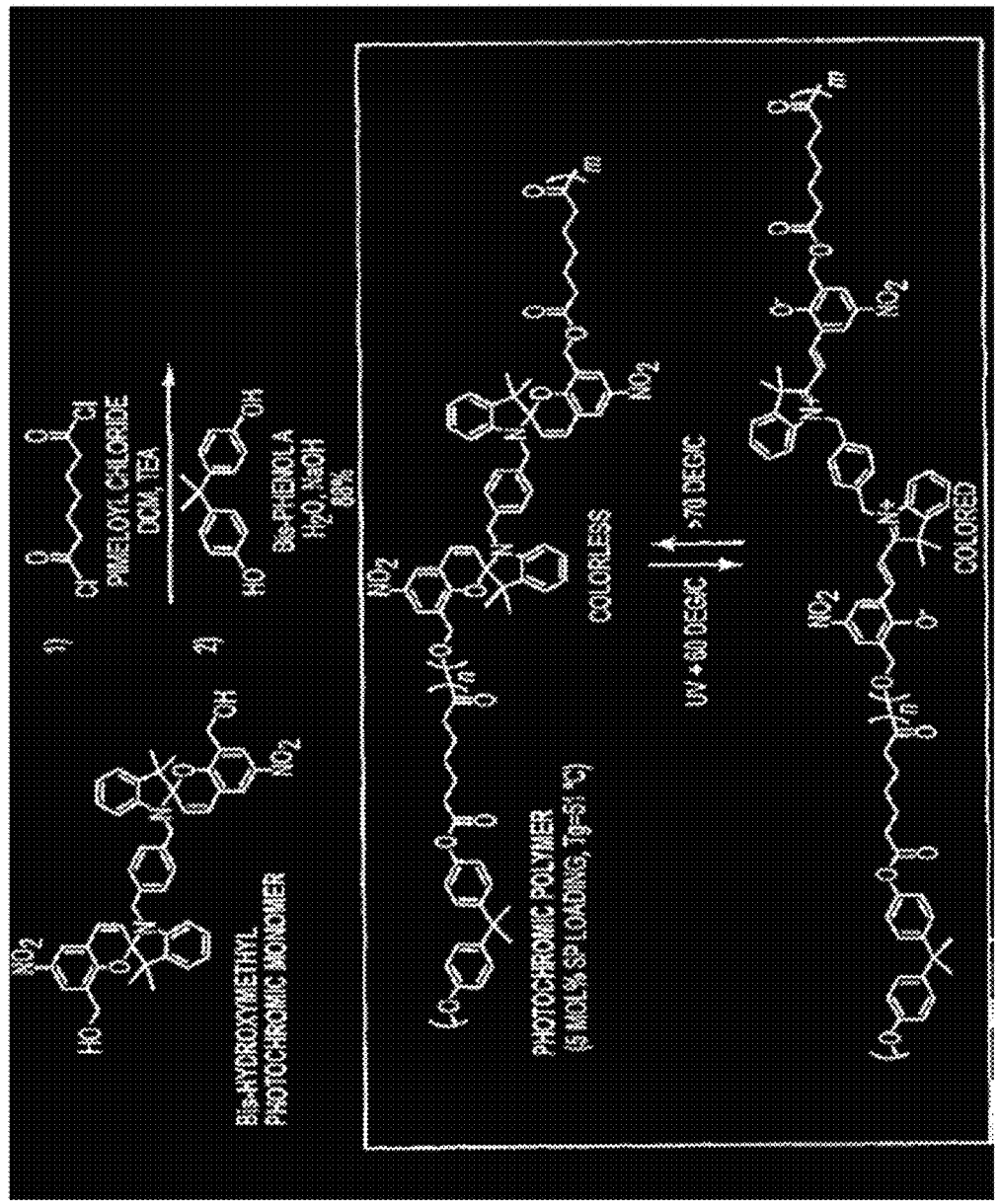
FIG. 10 depicts one embodiment of the synthesis of a photochromic polymer from the monomer of FIG. 9.

As described above, in some embodiments, the transition portions of the mask contain light-activated photochromic chromophores contained within a polymer matrix with a controlled Tg. In some embodiments, the photochromic chromophore is polymerized directly into the backbone of the polymer used in the polymer matrix. Suitable photochromic chromophores are described above, however, in some embodiments suitable polymers can be formed from first and second monomers. For example, further details concerning the formation of first and second monomers and incorporation of a photochromic chromophore into a polymer matrix can be found in U.S. Pat. No. 8,216,765, entitled "REIMAGEABLE AND REUSABLE MEDIUM AND METHOD OF PRODUCING AND USING THE REIMAGEABLE AND REUSABLE MEDIUM," filed Mar. 9, 2009 and which was incorporated by reference above. FIG. 9 illustrates one embodiment of a synthesis scheme for a photochromic monomer. FIG. 10 illustrates one embodiment of a synthesis scheme for the synthesis of a photochromic polymer from the co-polymerization of a photochromic monomer.

In certain embodiments, the photochromic polymer is optionally dissolved or dispersed in any suitable carrier, such as a solvent, a polymer binder, or the like. Water may be used as a solvent for water soluble photochromic polymers and water-soluble binders such as poly(vinyl alcohol) and poly(acrylic acid). Other suitable solvents include, for example, straight chain aliphatic hydrocarbons, branched chain aliphatic hydrocarbons, and the like, such as where the straight or branched chain aliphatic hydrocarbons have from about 1 to about 30 carbon atoms. For example, a non-polar liquid of the ISOPAR™ series (manufactured by the Exxon Corporation) may be used as the solvent. These hydrocarbon liquids are considered narrow portions of iso-paraffinic hydrocarbon fractions. Other suitable solvent materials include, for example, the NORPAR™ series of liquids, which are compositions of n-paraffins available from Exxon Corporation, the SOLTROL™ series of liquids available from the Phillips Petroleum Company, and the SHELL-SOL™ series of liquids available from the Shell Oil Company. Mixtures of one or more solvents, i.e., a solvent system, can also be used, if desired. In addition, more polar solvents can also be used, if desired. Examples of more polar solvents that may be used include halogenated and nonhalogenated solvents, such as tetrahydrofuran, trichloro- and tetrachloroethane, dichloromethane, chloroform, monochlorobenzene, toluene, xylenes, acetone, methanol, ethanol, xylenes, benzene, ethyl acetate, dimethylformamide, cyclohexanone, N-methyl acetamide and the like. The solvent may be composed of one, two, three or more different solvents. When two or more different solvents are present, each solvent may be present in an equal or unequal amount by weight ranging for example from about 5% to 90%, particularly from about 30% to about 50%, based on the weight of all solvents.

In some embodiments, the photochromic polymer can be dispersed in another, non-photochromic polymer binder. Such an additional polymer binder may be desired, for example, depending on the properties, characteristics, and the like of the photochromic polymer. Of course, it will be understood that an additional polymer binder may not be required in some embodiments, as the photochromic polymer can itself function as a binder material. Suitable examples of polymer binders that can be used include, but are not limited to, polyalkylacrylates like polymethyl methacrylate (PMMA), polycarbonates, polyethylenes, oxidized polyethylene, polypropylene, polyisobutylene, polystyrenes, poly(styrene)-co-(ethylene), polysulfones, polyethersulfones, polyarylsulfones, polyarylethers, polyolefins, polyacrylates, polyvinyl derivatives, cellulose derivatives, polyurethanes, polyamides, polyimides, polyesters, silicone resins, epoxy resins, polyvinyl alcohol, polyacrylic acid, and the like. Copolymer materials such as polystyrene-acrylonitrile, polyethylene-acrylate, vinylidenechloride-vinylchloride, vinylacetate-vinylidene chloride, styrene-alkyd resins are also examples of suitable binder materials. The copolymers may be block, random, or alternating copolymers. In some embodiments, polymethyl methacrylate or a polystyrene is the polymer binder, in terms of their cost and wide availability. The polymer binder, when used, has the role to provide a coating or film forming composition.

Phase change materials can also be used as the polymer binder. Phase change materials are known in the art, and include for example crystalline polyethylenes such as Polywax® 2000, Polywax® 1000, Polywax® 500, and the like from Baker Petrolite, Inc.; oxidized wax such as X-2073 and Mekon wax, from Baker-Hughes Inc.; crystalline polyethylene copolymers such as ethylene/vinyl acetate copolymers, ethylene/vinyl alcohol copolymers, ethylene/acrylic acid copolymers, ethylene/methacrylic acid copolymers, ethylene/carbon monoxide copolymers, polyethylene-b-polyalkylene glycol wherein the alkylene portion can be ethylene, propylene, butylenes, pentylene or the like, and including the polyethylene-b-(polyethylene glycol)s and the like; crystalline polyamides; polyester amides; polyvinyl butyral; polyacrylonitrile; polyvinyl chloride; polyvinyl alcohol hydrolyzed; polyacetal; crystalline poly(ethylene glycol); poly(ethylene oxide); poly(ethylene therephthalate); poly(ethylene succinate); crystalline cellulose polymers; fatty alcohols; ethoxylated fatty alcohols; and the like, and mixtures thereof.

In some embodiments, any suitable polymer that has one or more photochromic molecules or compounds bound to the polymer backbone, can be used. Such photochromic polymers can have the photochromic molecules or compounds covalently bound to the polymer backbone within the polymer chain itself. Such groups can be introduced into the polymer chain, for example, by including the photochromic molecules or compounds during the polymer preparation process, such as in the form of reactive units, monomer units, or the like, or they can be added to an already formed non-photochromic polymer material through known chemical functionalization reactions.

Where multiple photochromic molecules or compounds are present in the polymer chain, the multiple photochromic molecules or compounds can be the same or different. Likewise, the photochromic polymer can include only one type of photochromic polymer, or can include a mixture of two or more different types of photochromic polymer (such as different photochromic polymers having different photochromic molecules or compounds in the polymer chain, or the same or different photochromic molecules or compounds in different polymer chains. Because the photochromic polymer is converted between its colored and colorless states by the use of light and heat, the polymer and photochromic molecules or compounds are desirably selected such that the photochromic polymer has thermal properties that can withstand the elevated temperatures that may be used.

Figure 11:
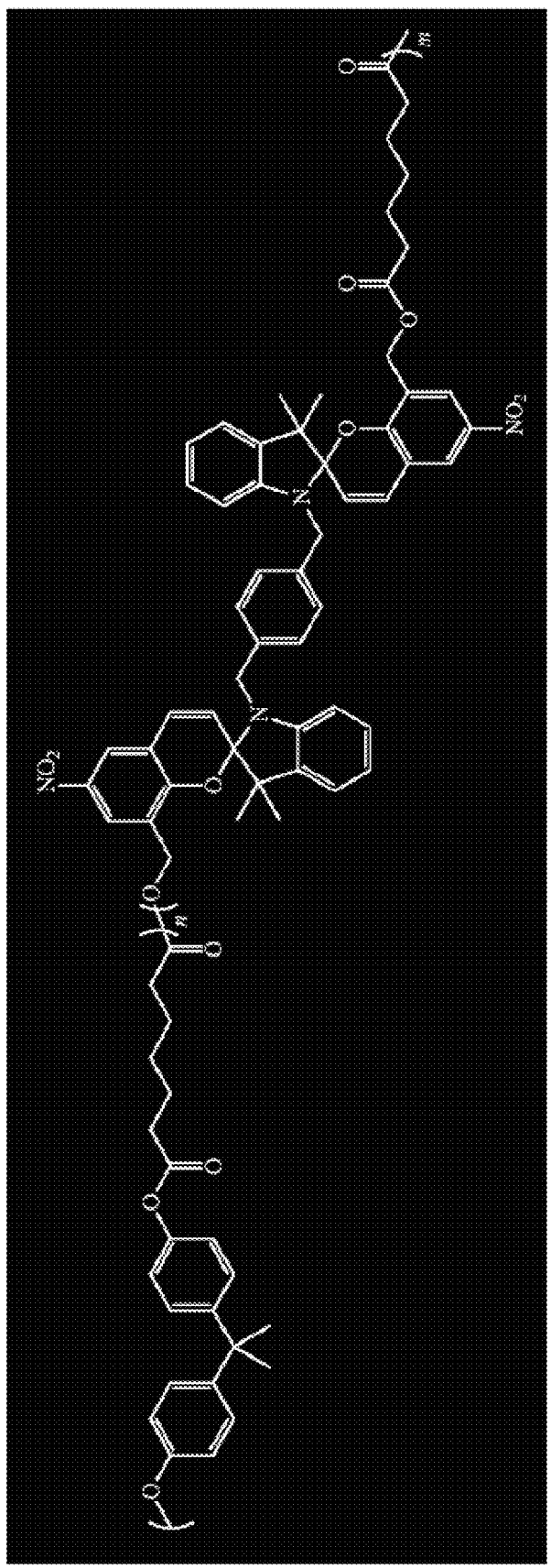
FIG. 11 depicts one embodiment of a general formula for a photochromic polymer.

FIG. 11 depicts an embodiment of a suitable incorporation of a photochromic chromophore into a polymer backbone. In this illustrative embodiment, the photochromic chromophore can be between a first and second monomer. Likewise, any suitable non-photochromic polymer materials may be selected for forming the non-photochromic parts of the photochromic polymer. Examples include, but are not limited to, the polymers described above as useful for a polymer binder. For example, in one embodiment, suitable polymers include those that can be formed from first and second monomers. The first monomer may be diacyl chlorides, diacids, its dimethyl esters, or its unhydrous cyclic esters such as oxalyl, malonyl, succinyl, glutaryl, adipoyl, pimeloyl, suberoyl, azelaoyl, sebacoyl, fumaryl, terephthalic, isophthalic, phthalic, and mixtures thereof, wherein the alkyl portion can be a straight, branched or cyclic, saturated or unsaturated, substituted or unsubstituted, from 1 to about 40 carbon atoms, a substituted or unsubstituted aromatic or heteroaromatic group. The second monomer may be bisphenols or diols such as Bis-phenol A, bisphenol B, bisphenol C, bisphenol F, bisphenol M, bisphenol P, bisphenol AP, bisphenol Z, ethylene glycol, propylene glycol, butylene glycol, pentylene glycol, hexylene glycol, heptylene glycoldiethylene glycol, dipropylene glycol, dipropylene glycol, cyclohexyldimethanol, bisphenol A ethoxylate, bisphenol A propoxylate, and mixtures thereof, wherein the alkyl portion can be a straight, branched or cyclic, saturated or unsaturated, substituted or unsubstituted, from 1 to about 40 carbon atoms, an substituted or unsubstituted aromatic or heteroaromatic group.

In certain embodiments, a photochromic polymer containing a photochromic chromophore within a polymer backbone is mixed with a second miscible polymer with side-chain crystallizable side groups such as polyoctadecyl acrylate. For example, further details concerning side-chain crystallizable polymers can be found in U.S. Pat. No. 4,830,855, entitled "TEMPERATURE-CONTROLLED ACTIVE AGENT DISPENSER," filed Nov. 13, 1987 and which is hereby incorporated by reference in its entirety. In certain embodiments, the photochromic chromophore can be polymerized directly into side-chain crystallizable polymers. In certain embodiments, the first and/or second monomers described above can be side-chain crystallizable polymers.

Figure 12:
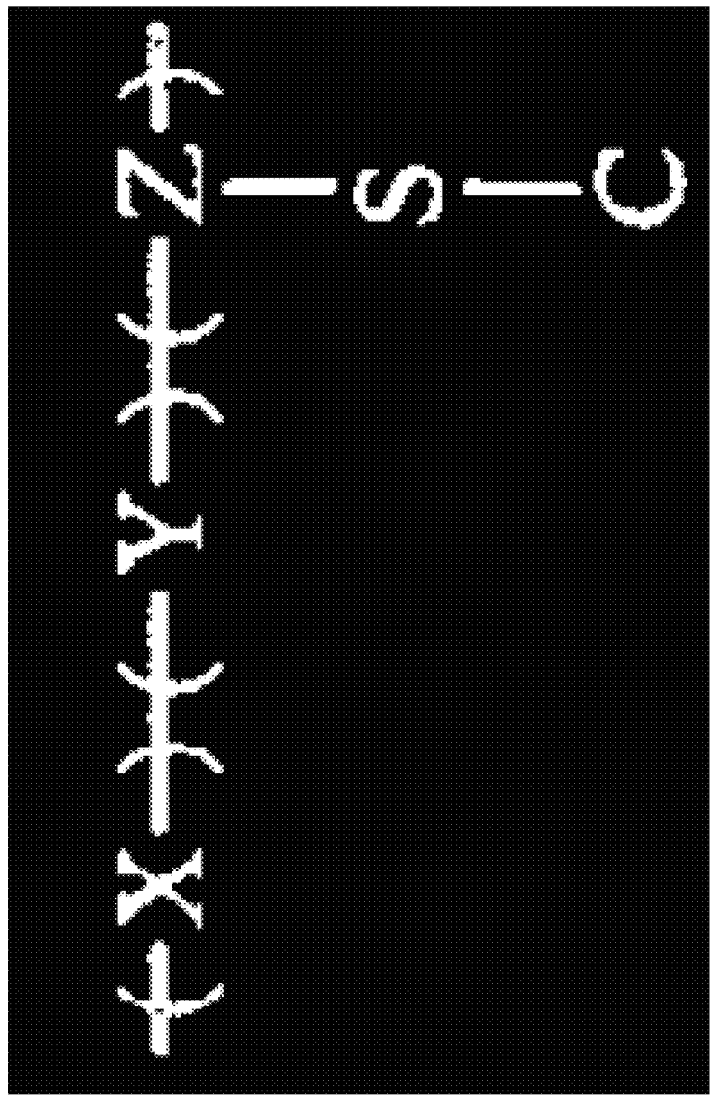
FIG. 12 depicts one embodiment of a side-chain crystallizable polymer.

FIG. 12 depicts an embodiment of a side-chain crystallizable polymer, where X is a first monomer unit, Y is a second monomer unit, Z is a backbone atom, S is a spacer unit and C is a crystallizable group. Side-chain crystallizable polymers, sometimes called "comb-like" polymers are well known and available commercially. These polymers are reviewed in J. Poly. Sci.: Macromol. Rev. (1974) 8: 117-253. In some embodiments the molecular weight of C is equal to or greater than twice the sum of the molecular weights of X, Y and Z. These polymers have a heat of fusion (~Ht) of at least about 5 calories/g, preferably at least about 10 calories/g. The backbone of the polymer (defined by X, Y and Z) may be any organic structure (aliphatic or aromatic hydrocarbon, ester, ether, amide, etc.) or an inorganic structure (sulfide, phosphazine, silicone, etc.). The spacer linkages can be any suitable organic or inorganic unit, for example ester, amide, hydrocarbon, phenyl, ether, or ionic salt (for example a carboxyl-alkyl ammonium or sulphonium or phosphonium ion pair or other known ionic salt pair). The side-chain (defined by S and C) may be aliphatic or aromatic or a combination of aliphatic and aromatic, but must be capable of entering into a crystalline state. Common examples are linear aliphatic side-chains of at least 10 carbon atoms, fluorinated aliphatic side-chains of at least 6 carbons, and p-alkyl styrene side-chains wherein the alkyl is of 8 to 24 carbon atoms.

In some embodiments, the length of the side-chain moiety is usually greater than 5 times the distance between side-chains in the case of acrylates, methacrylates, vinyl esters, acrylamides, methacrylamides, vinyl ethers and alpha olefins. In certain embodiments, a fluoroacrylate alternate copolymer with butadiene as the side-chain can be as little as 2 times the length as the distance between branches. In some embodiments, the side-chain units should make up greater than 50% of the volume of the polymer, preferably greater than 65% of the volume. Co-monomers added to a side-chain polymer usually have an adverse effect on crystallinity Small amounts of various co-monomers can be tolerated, usually up to 10 to 25 volume percent. In some embodiments, it is desirable to add small amounts of co-monomer, for example cure site monomers such as acrylic acid, glycidal methacrylate, maleic anhydride, amino function monomer and the like. Specific examples of side-chain crystallizable monomers are the acrylate, fluoroacrylate, methacrylate and vinyl ester polymers described in J. Poly. Sci. (1972) 10:50 3347; J. Poly. Sci. (1972) 10: 1657; J. Poly. Sci. (1971) 9:3367; J. Poly. Sci. (1971) 9: 3349; J. Poly. Sci. (1971) 9:1835; J.A.C.S. (1954) 76: 6280; J. Poly. Sci. (1969) 7: 3053; Polymer J. (1985) 17: 991. corresponding acrylamides, substituted acrylamide and maleimide polymers (J. Poly. Sci., Poly. Physics Ed. (1980) 18: 2197; polyalphaolefin polymers such as those described in J. Poly. Sci.: Macromol. Rev. (1974) 8: 117-253 and Macromolecules (1980) 13: 12, polyalkylvinylethers, polyalkylethylene oxides such as those described in Macromolecules (1980) 13: 15, alkylphosphazene polymers, polyamino acids such as those described in Poly. Sci. USSR (1979) 21: 241, Macromolecules (1985) 18: 2141, polyisocyanates such as those described in Macromolecules (1979) 12: 94. polyurethanes made by reacting amine- or alcohol-containing monomers with long chain alkyl isocyanates, polyesters and poly ethers. Polysiloxanes and polysilanes such as those described in Macromolecules (1986) 19: 611 and p-alkyl-styrene polymers such as those described in J.A.C.S. (1953) 75: 3326 and J. Poly. Sci. (1962) 60: 19.

In certain embodiments, the photochromic chromophore can be incorporated into a polyester polycondensate. For example, further details concerning this type of incorporation can be found in U.S. Pat. No. 3,918,972, entitled "IMAGING PROCESS UTILIZING A POLYESTER POLYCONDENSATE CONTAINING SPIROPYRAN PHOTOCHROMIC GROUPS" filed Aug. 13, 1973 and hereby incorporated by reference in its entirety. Further details concerning additional photochromic polycondensates can be found in U.S. Pat. No. 4,026,869 entitled PHOTOCHROMIC POLYCONDENSATES, filed Jul. 21, 1975 and hereby incorporated by reference in its entirety.

In some embodiments, linear polycondensates of the polyester type are provided characterized in that they contain spiropyran photochromic groups as an integral part of the main polymer chain. In certain embodiments, they can be prepared by polycondensation of Bisphenol-A and a photochromic compound carrying a hydroxyalkyl group on either side of the photochromic moiety, with a dicarboxylic acid of the saturated dicarboxylic acid series, preferably with succinic acid, adipic acid, glutaric acid and pimelic acid. In this process the dicarboxylic acid in the form of a diacid dichloride is dissolved in an organic liquid, such as methylene chloride, dichloroethane, tetrachloroethane, benzene or toluene, which is also a solvent for the copolycondensate to be formed. The bisphenol is dissolved in another liquid, which is immiscible with the above organic liquid. Preferably water is used as a solvent for the bisphenol and an equivalent amount of a metal hydroxide, such as sodium hydroxide or potassium hydroxide is added to the water in order to form immediately the corresponding diphenolate. The reaction speed is greatly increased by using quaternary ammonium compounds as catalysts. The two solutions are mixed and stirred vigorously at the reaction temperature, whereby the copolyester is formed in solution. In the same way the photochromic copoly-condensates of the invention are formed. In some embodiments, a photochromic compound carrying on either side of the photochromic moiety an hydroxyalkyl group is made to react with an excess of the diacid dichloride e.g. of succinic acid, adipic acid, glutaric acid, or pimelic acid, and the photochrome-bis-acid chloride formed in this way is made to react in a two-phase reaction mixture with a diphenolate of bisphenol-A. Suitable photochromic compounds carrying two hydroxyalkyl groups on either side of the photochromic moiety are compounds, containing spiropyran groups.

In certain embodiments, the photochromic chromophore is directly polymerized into a polymer backbone as described above and mixed with the miscible polymer combination described above. In some embodiments, the photochromic dye is directly polymerized into the polymer backbone of a polymer that also has side chain crystallizable side groups such as described above. In certain embodiments, the photochromic oligomers or monomers described above and in U.S. Pat. No. 8,216,765 can be mixed with the aforementioned miscible combination of polymers. In some embodiments, a dimer of any of the aforementioned photochromic chromophores can be mixed with any of the aforementioned polymers.

In further embodiments, the Tg of the polymer matrix can be between 30°-150° C. For example, the Tg can be at least about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about 150° C.

The Tg of the polymer matrix can be varied by changing the chemical properties of the polymers comprising the polymer matrix. In some embodiments, the Tg of the polymer matrix can be modified by varying the chain length of the monomer used in polymerization. In further embodiments, the Tg is controlled by varying the chain length of the side groups that branch from the polymer backbone. In other embodiments, the Tg of the polymer matrix can be adjusted by varying the spacing between the side-chains. In certain embodiments, the Tg of the polymer is controlled by varying the cross-link density of the polymer. In other embodiments, the Tg of the polymer can be controlled by varying the molecular weight of the polymer. Any of the aforementioned polymer properties can be adjusted together or separately to tune the Tg of the polymer matrix.

As described previously, in some embodiments, heat can be used to cause the polymer matrix to undergo a glass transition. In certain embodiments, heat is provided to the polymer matrix via focused radiant energy from outside the eye. For example, this focused radiant energy can be a laser. In some embodiments, ultrasonic energy can be applied to the mask to heat it. In some embodiments, heat or other initiator is applied to the transition portions, or to one of multiple transition portions of the mask.

In some embodiments, an axicon lens can be used to focus a circular beam of radiant energy into the eye and onto a mask to heat an annular area of the mask inside the eye. In certain embodiments, the annular pattern created by the axicon lens can be focused further before entering the eye to create a confocal focusing of the annular pattern to bring it to a smaller, higher energy density annular region of focus inside the eye on the mask. In certain embodiments, a biconvex toric lens could be used to achieve the confocal focusing of the annular pattern output from the axicon lens element to focus it confocally into the eye. In some embodiments, other optical configurations instead of an axicon lens can be used to provide a confocally focused annular beam of energy into the eye.

In some embodiments, focusing of the radiant energy into the eye and onto the mask would be completed with simultaneous microscope viewing for better control and monitoring of the procedure inside the eye. This arrangement is advantageous, as the focus of the radiation area on the mask and the change of the photochromic chromophores in this area could be directly observed.

While the above detailed description has shown, described, and pointed out novel features as applied to various embodiments, it will be understood that various omissions, substitutions, and changes in the form and details of the device or process illustrated can be made without departing from the spirit of the disclosure. As will be recognized, certain embodiments of the inventions described herein can be embodied within a form that does not provide all of the features and benefits set forth herein, as some features can be used or practiced separately from others. The scope of the inventions is indicated by the appended claims rather than by the foregoing description. All changes which come within the meaning and range of equivalency of the claims are to be embraced within their scope.

What is claimed is:

1. An ophthalmic device, comprising:
an intraocular mask comprising an aperture configured to transmit substantially all visible light along the optical axis of the eye, the aperture configured to switch between a first size and a second size in response to application of an external stimulus; and
wherein the aperture is configured to remain locked into the second size after removal of the external stimulus until another application of the external stimulus, the aperture then returning to the first size.

2. The ophthalmic device of claim 1, further comprising an intraocular lens coupled to the intraocular mask.

3. The ophthalmic device of claim 1, wherein the intraocular mask comprises a plurality of photochromic chromophores within a polymer matrix.

4. The ophthalmic device of claim 3, wherein the plurality of photochromic chromophores are distributed homogenously.

5. The ophthalmic device of claim 3, wherein the plurality of photochromic chromophores are distributed heterogeneously.

6. The ophthalmic device of claim 3, wherein the concentration of photochromic chromophores varies within the polymer matrix to result in a range of opacities within the intraocular mask.

7. The ophthalmic device of claim 3, wherein the plurality of photochromic chromophores comprise spiropyran.

8. The ophthalmic device of claim 1, wherein the external stimulus is chosen from the group consisting of light, heat, and electrical current.

9. The ophthalmic device of claim 1, wherein the external stimulus comprises heat provided by a laser.

10. The ophthalmic device of claim 1, wherein the external stimulus comprises radiant energy focused through an axicon lens.

11. The ophthalmic device of claim 1, wherein the external stimulus is provided by light primarily in a wavelength chosen from the group of ultraviolet light, infrared light, and visible light.

12. The ophthalmic device of claim 1, wherein the mask is configured to switch between the first size, the second size, and a third size in response to an external stimulus.

13. The ophthalmic device of claim 1, wherein the aperture is surrounded by a first annular zone.

14. The ophthalmic device of claim 13, wherein the first annular zone is configured to switch between a first level of opacity and a second level of opacity in response to application of the external stimulus.

15. The ophthalmic device of claim 14, further comprising a second annular zone.

16. The ophthalmic device of claim 15, wherein the second annular zone is configured to block transmission of substantially all visible light.

17. The ophthalmic device of claim 15, wherein the second annular zone is configured to switch between a third level of opacity and a fourth level of opacity in response to application of the external stimulus.

18. The ophthalmic device of claim 17, wherein the first and second annular zones comprise a plurality of photochromic chromophores within a polymer matrix.

19. The ophthalmic device of claim 18, wherein the photochromic chromophores are distributed homogenously.

20. The ophthalmic device of claim 18, wherein the photochromic chromophores are distributed heterogeneously.

21. The ophthalmic device of claim 18, wherein the first annular zone comprises a first concentration of photochromic chromophores and the second annular zone comprises a second concentration of photochromic chromophores.

22. An intraocular mask, comprising:
- an aperture configured to transmit substantially all visible light along the optical axis of the eye;
- a first annular zone surrounding the aperture, the first annular zone configured to switch between a first level of opacity and a second level of opacity in response to application of an external stimulus;
- wherein the first annular zone is configured to remain locked into the second level of opacity after removal of the external stimulus until another application of the external stimulus, the first annular zone then returning to the first level of opacity; and
- a second annular zone surrounding the aperture, the second annular zone configured to block transmission of substantially all visible light.

* * * * *

UNITED STATES PATENT AND TRADEMARK OFFICE
CERTIFICATE OF CORRECTION

PATENT NO. : 10,350,058 B2
APPLICATION NO. : 15/436150
DATED : July 16, 2019
INVENTOR(S) : Thomas Silvestrini Page 1 of 3

It is certified that error appears in the above-identified patent and that said Letters Patent is hereby corrected as shown below:

On the Title Page

Column 2, Item (56), Line 1, under Other Publications, delete "Accomodation" and insert --Accommodation--.

On Page 8, Column 1, Item (56), Lines 1-2, under Other Publications, delete "Opthalmology" and insert --Ophthalmology--.

On Page 8, Column 1, Item (56), Line 3, under Other Publications, delete "Accomodation" and insert --Accommodation--.

On Page 8, Column 2, Item (56), Line 6, under Other Publications, delete "accomodation." and insert --accommodation.--.

On Page 8, Column 2, Item (56), Line 29, under Other Publications, delete "Hydrophopic" and insert --Hydrophobic--.

On Page 8, Column 2, Item (56), Line 30, under Other Publications, delete "Light-Absorving" and insert --Light-Absorbing--.

On Page 8, Column 2, Item (56), Line 37, under Other Publications, delete "Hydrophopic" and insert --Hydrophobic--.

On Page 8, Column 2, Item (56), Line 37, under Other Publications, delete "Absorving" and insert --Absorbing--.

On Page 9, Column 1, Item (56), Lines 4-5, under Other Publications, delete "Opthalmology," and insert --Ophthalmology,--.

Signed and Sealed this
Twenty-sixth Day of November, 2019

Andrei Iancu
*Director of the United States Patent and Trademark Office*

CERTIFICATE OF CORRECTION (continued)
U.S. Pat. No. 10,350,058 B2

On Page 9, Column 1, Item (56), Line 41, under Other Publications, delete "Opthalmology," and insert --Ophthalmology,--.

On Page 9, Column 2, Item (56), Line 16, under Other Publications, delete "flouride" and insert --fluoride--.

On Page 9, Column 2, Item (56), Line 42, under Other Publications, delete "Opthalmology," and insert --Ophthalmology,--.

On Page 9, Column 2, Item (56), Line 56, under Other Publications, delete "Opthalmology," and insert --Ophthalmology,--.

On Page 10, Column 1, Item (56), Line 25, under Other Publications, delete "Manfacturing" and insert --Manufacturing--.

On Page 10, Column 1, Item (56), Line 28, under Other Publications, delete "jan/ago" and insert --jan/aug--.

On Page 10, Column 2, Item (56), Line 2, under Other Publications, delete "prosepective" and insert --prospective--.

On Page 10, Column 2, Item (56), Line 17, under Other Publications, delete "Opthalmology," and insert --Ophthalmology,--.

On Page 10, Column 2, Item (56), Line 35, under Other Publications, delete "Keratoplosty:" and insert --Keratoplasty:--.

On Page 10, Column 2, Item (56), Lines 35-36, under Other Publications, delete "Cyropreservation,"" and insert --Cryopreservation,"--.

In the Specification

In Column 3, Lines 64-65, delete "polysulfone)," and insert --polysulfone,--.

In Column 9, Line 1, delete "FIG." and insert --FIGS.--.

In Column 13, Line 67, delete "therephthalate);" and insert --terephthalate);--.

In Column 14, Line 1, delete "therephthalate);" and insert --terephthalate);--.

In Column 14, Line 21, delete "(such" and insert --such--.

In Column 14, Line 42, delete "unhydrous" and insert --anhydrous--.

In Column 14, Line 50, delete "Bis-phenol" and insert --bisphenol--.

CERTIFICATE OF CORRECTION (continued)
U.S. Pat. No. 10,350,058 B2

In Column 15, Line 44, delete "crystallinity" and insert --crystallinity.--.

In Column 15, Lines 48-49, delete "glycidal" and insert --glycidyl--.

In Column 15, Line 56, delete "991." and insert --991;--.

In Column 15, Line 58, delete "(J." and insert --J.--.

In Column 15, Line 66, delete "94." and insert --94,--.

In Column 16, Line 22, delete "Bisphenol-A" and insert --bisphenol-A--.